United States Patent [19]

Riggs et al.

[11] Patent Number: 5,355,872
[45] Date of Patent: Oct. 18, 1994

[54] LOW FLOW RATE NEBULIZER APPARATUS AND METHOD OF NEBULIZATION

[76] Inventors: John H. Riggs, 201-F Foliage Cir., Cary, N.C. 27511; Barry O. Mangum, P.O. Box 20554, Raleigh, N.C. 27619

[21] Appl. No.: 927,834

[22] Filed: Aug. 10, 1992

Related U.S. Application Data

[63] Continuation-in-part of Ser. No. 846,784, Mar. 4, 1992, Pat. No. 5,186,166.

[51] Int. Cl.$^5$ .............. A61M 11/00; A61M 16/10; B05B 1/26; B05D 7/14
[52] U.S. Cl. ............. 128/200.21; 128/203.12; 128/200.18; 128/203.15; 239/338
[58] Field of Search ........... 128/200.14, 200.18, 128/200.19, 200.21, 203.15, 203.12, 203.19, 203.21, 203.24, 203.25, 203.29; 239/290 R, 2903, 149, 338

[56] References Cited

U.S. PATENT DOCUMENTS

| | | |
|---|---|---|
| 2,792,971 | 5/1957 | Kaiser . |
| 3,172,406 | 3/1965 | Bird et al. .................. 128/200.18 |
| 3,353,873 | 11/1967 | Dietert . |
| 3,658,059 | 4/1972 | Steil . |
| 3,809,080 | 5/1974 | Deaton .................... 261/78 |
| 3,864,326 | 2/1975 | Babington ................. 239/338 |
| 3,874,379 | 4/1975 | Enfield et al. . |
| 4,054,622 | 10/1977 | Lester ..................... 128/200.18 |
| 4,094,318 | 6/1978 | Burke et al. ............... 128/DIG. 13 |
| 4,098,853 | 7/1978 | Brown et al. ............... 261/122 |
| 4,195,044 | 3/1980 | Miller ..................... 261/142 |
| 4,197,843 | 4/1980 | Bird ...................... 128/200.14 |
| 4,268,460 | 5/1981 | Boiarski et al. ............ 128/200.21 |
| 4,275,726 | 6/1981 | Schael . |
| 4,276,876 | 7/1981 | Hakkinen ................... 128/200.14 |
| 4,344,574 | 8/1982 | Meddings et al. ............ 128/200.18 |
| 4,462,397 | 7/1984 | Suzuki ..................... 128/200.14 |
| 4,509,943 | 4/1985 | Hanzawa ................... 604/31 |
| 4,541,966 | 9/1985 | Smith ...................... 261/27 |
| 4,546,794 | 10/1985 | Ball ....................... 137/599 |
| 4,588,129 | 5/1986 | Shanks ..................... 128/200.18 |
| 4,598,704 | 7/1986 | Bordoni et al. ............. 128/200.14 |
| 4,657,007 | 4/1987 | Carlin et al. .............. 128/200.18 |
| 4,662,799 | 5/1987 | Paul et al. ................ 406/14 |

(List continued on next page.)

FOREIGN PATENT DOCUMENTS

| | | |
|---|---|---|
| 835910 | 6/1981 | U.S.S.R. . |
| 1418218 | 8/1988 | U.S.S.R. . |
| 2164569 | 3/1986 | United Kingdom . |
| 8606969 | 12/1986 | World Int. Prop. O. . |

OTHER PUBLICATIONS

Raabe, O. G., et al A Signal Actuated Nebulizer for use with Breathing Machines, Journal of Aerosol Medicine, vol. 2, No. 2, 1989, pp. 201–210.

Simonds, A. K. et al, Simple Nebuliser Modification to Enhance Alveolar Deposition of Pentamidine, The Lancet, Oct. 21, 1989 p. 953.

(List continued on next page.)

Primary Examiner—Kimberly L. Asher
Attorney, Agent, or Firm—Steven J. Hultquist

[57] ABSTRACT

A nebulizer device, comprising: (a) a housing defining an interior volume therewithin, including a reservoir portion for holding medicament therein for entrainment into a carrier gas to form a delivery gas mixture comprising nebulized medicament and carrier gas; (b) a discharge port connected to the housing in flow communication with the interior volume therewithin, for discharging the delivery gas mixture from the housing; (c) a jet passage member having (i) an inlet portion for introduction of carrier gas thereinto and (ii) a nozzle portion positioned in the interior volume of the housing for discharging carrier gas in jet form in the interior volume, for entrainment of medicament from the reservoir portion of the housing in the carrier gas jet, such nozzle portion comprising a nozzle orifice accommodating carrier gas flow therethrough, wherein the nozzle orifice has an equivalent orifice diameter in the range of from about 0.005 inch to about 0.020 inch.

14 Claims, 6 Drawing Sheets

U.S. PATENT DOCUMENTS

| | | | |
|---|---|---|---|
| 4,674,491 | 6/1987 | Brugger et al. | 128/200.14 |
| 4,682,010 | 7/1987 | Drapeau et al. | 128/203.27 |
| 4,703,753 | 11/1987 | Bordoni et al. | 128/200.14 |
| 4,758,117 | 7/1988 | Maki et al. | 406/14 |
| 4,805,609 | 2/1989 | Roberts et al. | 128/200.21 |
| 4,832,012 | 5/1989 | Raabe et al. | 128/200.21 |
| 4,838,856 | 6/1989 | Mulreany et al. | 604/65 |
| 4,920,336 | 4/1990 | Meijer | 340/619 |
| 4,921,642 | 5/1990 | LaTorraca | 128/203.27 |
| 4,938,209 | 7/1990 | Fry | 128/200.21 |
| 4,946,439 | 8/1990 | Eggers | 604/67 |
| 4,950,245 | 8/1990 | Brown et al. | 604/153 |
| 5,025,829 | 6/1991 | Edwards et al. | 137/512 |
| 5,080,093 | 1/1992 | Raabe et al. | 128/203.12 |
| 5,086,765 | 2/1992 | Levine | 128/200.21 |
| 5,119,807 | 6/1992 | Roberts et al. | 128/200.24 |
| 5,186,166 | 2/1993 | Riggs et al. | 128/203.15 |
| 5,287,847 | 2/1994 | Piper et al. | 128/200.21 |

OTHER PUBLICATIONS

Heart–High output Extended Aerosol Respiratory Therapy, product sheet of Vortran Medical Technology, Inc. Copyright 1989, 1 page.

Aerosol Therapy for Continuous Bronchodilation—Bradley Chipps, Md. Updates in Cardio–Pumonary Medicine, Nov. 16, 1989, 16 pages.

Portnoy, J., et al, Continuous terbutaline nebulization for the treatment of severe exacerbations of asthma in children, Annals of Allergy, vol. 60, Apr., 1988, pp. 368–371.

Jasper, A. C. et al, Cost–Benefit Comparison of Aerosol Bronchodilator Delivery Methods in Hospitalized Patients, Chest, vol. 91, No. 4 Apr. 1987, pp. 614–618.

Colacone, A., et al, Continuous Nebulization of Albuterol (Salbutamo) in Acute Asthma, Chest. vol. 97, No. 3, Mar. 1990, pp.693–697.

U.S. Patent issued Nov. 6, 1990 to R. C. Lambert. (Abstract).

"Respiratory Therapy Equipment," McPherson, Steven T., Second edition, C. V. Mosby, St. Louis, pp. 149–153, 1981.

"Neonatal PFTs and Mechanical Ventilation/A Cast Study," Riggs, John H., Neonatal Intensive Care, Sep.-/Oct. 1991, pp. 44–45.

"Low Flow," Riggs J. Neonatal Intensive Care, May/-Jun. 1991, p. 6.

LOW FLOW RATE NEBULIZER APPARATUS AND METHOD OF NEBULIZATION

CROSS-REFERENCE TO RELATED APPLICATION

This application is a continuation-in-part of U.S. patent application Ser. No. 07/846,784 filed Mar. 4, 1992, now U.S. Pat. No. 5,186,166.

BACKGROUND OF THE INVENTION

1. Field of the Invention

The present invention relates to a low flow rate nebulization method and a low flow rate nebulizer apparatus used in respiratory care and, in particular, to a continuously connected, continuous low gas flow rate liquid nebulizer useful in respiratory care to deliver liquid medications.

2. Description of the Related Art

Crtically ill patients requiring mechanical ventilation are often victims of respiratory distress syndrome, status asthamaticus and pulmonary infections. Treatment of these and other severe respiratory conditions includes medications delivered directly to the lungs of the patient.

Respiratory delivery of medication for these conditions is preferable to oral, intravenous and subcutaneous delivery because it is non-invasive, permits rapid action of medicament, requires a relatively small dosage, is not filtered through the liver of the patient, and produces a low incidence of systemic side effects.

Nebulized or aerosolized solutions are the preferred method of respiratory delivery of medication; when fragmented into small particles, medicants are more efficiently deposited near sites of medicant activity in the lung.

Respiratory medications may be delivered to the lungs of the patient as an aerosol of a liquid or a powder. Clinical aerosols are currently generated by jet or ulrasonic nebulizers, metered dose inhalers (MDI) and dry powdered inhalers.

Liquid nebulizers are well known in the art. Aerosolization of liquid medications is preformed by putting a liquid product in a chamber (nebulizer vial) that has a pressurized flow of gas through it. Utilizing the Bernoulli principle, liquid is drawn through an aspirator tube into the path of a high velocity gas and is fractured into a mist. The mist flows out of the nebulizer by inertial forces.

There are two principal types of nebulizers for the delivery of liquid medication to the lungs: jet nebulizers and ultrasonic nebulizers. In conventional jet nebulizers, compressed gas from a compressor or hospital air line is passed through a narrow constriction known as a jet. This creates an area of low pressure, and liquid medication from a reservoir is drawn up through a feed tube and fragmented into droplets by the airstream. Only the smallest drops leave the nebulizer directly, while the majority impact on baffles and walls and are returned to the reservoior. Consequently, jet nebulization takes several minutes to complete, depending upon the initial volume.

Important disadvantages of nebulizers include low lung deposition related to the use of tidal breathing. A substantial portion of the dose used in a jet nebulizer is retained permanently as a dead or residual volume on baffles and internal walls of the nebulizer chamber and cannot be released. Generally only 2–10% of the dose placed in the nebulizer ever reaches the lung. The consequences are a higher drug dosage and longer administrative time, along with the associated cost and risk of contamination.

Current conventional liquid aerosol drug therapy involves administering a finite quantity (dose) of liquid medication deposited into the nebulizer vial and administered until the vial is empty. In normal practice, the period of delivery of each dose is measured in minutes or fractions of an hour. Depending upon the severity of the illness and the duration of activity of the medication, this process is repeated periodically at variable frequencies.

Such intermittent drug administration has the inherent results of (1) subjecting the patient to "peaks and "valleys" of drug dosage effects, (2) requiring respiratory therapy personnel to periodically service the needs of the patient and nebulizer by measuring doses, disconnecting, filling and reconnecting the nebulizer and periodically monitoring the administration, and (3) disconnecting the patient from an attached ventilator during nebulizer service. Further, medication which is administered as a large volume, such as a surfactant, now requires large medicant flow volume through the nebulizer requiring frequent servicing and refilling of the nebulizer vial which interferes with ventilator function.

In some cases, a significant proportion of the respiratory flow to the patient is through the nebulizer such as in the operational use of the VISAN nebulizer of Burroughs Wellcome Company. In the delivery of the medicant EXOSURF® surfactant, up to half of the tidal volume flows through the nebulizing ports of the nebulizer to unite with the balance of the respiratory gas delivered directly from the ventilator in a Y-shaped junction in the flow path to the patient downstream from the nebulizer. In such delivery, the nebulizing gas is synchronized with the nebulizer such that nebulizing gas is delivered to the nebulizer only during the ventilatory inhalation cycle.

A nebulizer comprising a vial-like nebulizing chamber which comprises a two-position flow control valve assembly for accessibly draining and refilling the nebulizing chamber is disclosed in U.S. Pat. No. 4,805,609. While the valve assembly provides access for resupplying a medication close while the nebulizing chamber remains in sealed relation with the nebulizer, such resupply is service intensive and limited to volumes containable by the nebulizing chamber.

Recent developments in respiration therapy involve aersolization and delivery of nebulized mist on a continuous basis over several hours. For example, an entire day's medication dosage is delivered at a constant rate over twenty-four hours, as opposed to conventionally delivering the same dosage as four separate aliquots at six hour intervals. Such delivery eliminates the "peak" and "valleys" effects of the drug, reduces respiratory personnel suport times, and also reduces the number of time critical medication/nebulizer interconnections are interrupted, thereby diminishing the potentially dangerous exposures of the patient to the effects of respiratory circuit contamination.

Delivery of medicated mist is both in combination with a ventilator and through masks, mouthpieces, and other voluntary mist inhalation apparatus.

The second type of aerosol generator is a metered dose inhalator (MDI), which delivers a bolus of more concentrated drug aerosols than the solution commonly available for nebulizers. For optimal effect, MDI delivery systems require proper administration technique, which includes coordinated actuation of aerosol delivery with inhalation, a slow inhalation of 0.5–0.75 liters per second, a deep breath approaching inspiratory capacity inhalation, and at least 4 seconds of breath holding.

Many patients find it difficult to properly administer medication with an MDI, especially during acute exorbation. An article which appeared in *Eur. J. Respit. Dis.*, 68(5), 332 (1986), entitled "Bronchodilator Effects of a Fenoterol Meter Dose Inhaler and Fenoterol Powder in Asthmatics with Poor Inhaler Technique," described test findings showing that the effectiveness of bronchodilator medication, when delivered with an MDI, is dependent on good MDI technique. The article suggested that delivery of medication in a powdered form is more reliable for patients who do not exercise proper MDI technique.

MDIs can be equipped with devices that automatically couple actuation to inspiratory effort, thus eliminating the need for coordinating hand action with inhalation. Devices such as spacers and holding chambers also decrease partial velocity and reduce the number of large particles. Both of these features reduce oral pharyngeal and large airway deposition with a consequent reduction in systemic absorption. Deposition of aerosols from an MDI with a spacer or holding chamber is similar and perhaps better than the deposition of a properly used MDI alone.

Advantages of the MDI include deposition of 10–15% of the metered dose with consequent short treatment time, low cost and increased convenience. However, MDIs cannot be used by patients requiring mechanical ventilation. Other disadvantages include the need for patient cooperation, the practical limitations and inconveniences associated with increased dosing requirements due to the typically small dosages administered with an MDI, the limited number of currently available drugs, and the dependence on fluorocarbons of aerosol generation.

Others have recognized the need for new inhalation devices such as modified dry powder inhalers to replace use of MDIs due to environmental concerns related to the use of fluorocarbons. See "Today's Treatment of Airway Obstruction . . . and Tomorrow's?" Flenley, D. C., *Respiration*, 55 Suppl. 2, 4 (1989).

The third type of aerosol generator is a dry powder inhaler. Dry powdered inhalation devices currently in use are the Spinbaler, the Rotahaler, the Turbohaler and the disc inhaler. Dry powdered inhalers are breath actuated and usually require a higher inspiratory flow rate than that required for an MDI or a nebulizer. Flow rates of 1–2 liters per second are usually considered optimal, although flow rates as low as 0.5 liters per second may be effective for some dry powdered inhalers.

Advantages of dry powdered inhalers include relative ease of administration and the fact that they do not require fluorocarbon propellants. When a dry powdered inhaler is used properly, deposition appears to be similar to that of a properly used MDI.

However, powdered inhalers are limited by the dose they can provide and by the number of drugs currently available. Only terbutaline, salbutamol, dexamethasone and chromolyn sodium are available in powder form.

All conventional powder inhaler delivery systems utilize single dose capsules except the Turbohaler for administration of terbutaline. While several devices have been developed which permit preloading of several single dose capsules, neither these devices nor the Turbohaler have eliminated the other disadvantages of conventional powdered inhalers. See "A New Inhalation System for Bronchodilation. Study of the Acceptance of the Ingelheim M Inhaler in Chronic Obstructive Respiratory Tract Disease." Mutterlein, B. Schmidt, B., Fleisher, W., and Freund, D., *Fortschr. Med.*, April 15, 108(11), 225 (1990); "In Vivo Evaluation of the New Multiple Dose Powder Inhaler and the Rotahaler Using the Gamma Scintigraphy," Vidaren, M., Paronen, P., Vidaren, P. Vainir, P., and Nuutinen, J., Acta. *Pharm. Nord.*, 2(1), 3 (1990); "Clinical Use of Dry Powder Systems," Crompton, G. K., *Eur. J. Respir. Dis. Suppl.*, 122, 96 (1962).

Other disadvantages of dry powdered inhalers include the following: a) they are usually not particle size-selective and thus heavy oral pharyngeal deposition may occur; b) high humidity environments may cause clumping of the particles; and c) dry powdered inhalers cannot be used in ventilatory circuits.

Currently available devices for delivery of powdered medications to respiratory therapy do not employ nebulization technology.

The use of compressed air powered jet mills as a power generator for inhalation experiments is disclosed in "Use of a Jet Mill for Dispersing Dry Powder for Inhalation Studies," Cheng, Y. S., Marshall, T. C., Henderson, R. R., and Newton, G. J., *Am. Ind. Hya. Assoc. J.,* 46(8), 449 (1985). The jet mill consisted of an elongated channel), one material delivery jet, and two high speed air jets. Powder fed into the channel was dispersed by turbulence and centrifugal forces. The powder used in the inhalation experiments consisted of dye materials to be tested for toxicity. A flow rate of 400 liters per minute was maintained. The article does not address nebulization of powdered medication for purposes of respiratory therapy.

U.S. Pat. No. 4,232,002 discloses procedures for administering antihistamines. Methods disclosed include inhalation by a patient of mist, nebulized spray, or a cloud of fine solid particles. Products for delivery of medication include pressurized canistor inhalers, portable dry powder insuffilators using capsules, and nebulizers. The only dry powder delivery system described is a dry powder inhaler using capsules of dry powder in single dose units. The delivery method described involves puncturing a capsule of dry powder medication which is dispersed by means of a turbomixer to be inhaled thorugh a mouth piece. This patent does not address continuous flow or continuous delivery of inhalable medication. It does not enablingly teach or address jet nebulization of powdered solid medications, and does not teach a nebulizer vial which connects to a nebulizer to provide a device for introducing continuous flow.

U.S. Pat. No. 3,669,113 discloses a method and device for dispensing powdered medication from a perforated container by rotating the container by pneumatic means and causing the axis of rotation of the container to precess and describe a path of precession which is contained within a generally conical surface of a precession. The mechanisms described are based on varying shaft and bearing configurations. The method of this patent is said to be especially well suited to delivery of particles less than 80 microns in diameter. The patent does not address jet nebulization, continuous flow or continuous nebulization.

Recent developments in respiration therapy involve aerosolization and delivery of nebulized liquids on a continuous basis over several hours. Such delivery stabilizes the effects of the medication over time, reduces respiratory personnel support time, and reduces the chances of respiratory circuit contamination.

In our prior co-pending U.S. patent application Ser. No. 07/729,518, filed Jul. 12, 1991, a liquid nebulizer system is disclosed comprising a nebulizer attachable nebulizer vial, a large supply vessel, and a fluid delivery system, to be used with a conventional liquid nebulizer. The liquid nebulizer system provides for continuous delivery of liquid medication from a large supply vessel into the nebulizer vial which is attached to a conventional nebulizing apparatus, permitting continuous delivery of nebulized liquid medication. The disclosure of such prior copending application is hereby incorporated herein by reference.

In conventional, commercially available liquid nebulizer systems, a carrier gas flow rate in the range of from about 6 to about 8 liters per minute is used. Such flow rate range is necessary for conventional nebulizer devices to operate with suitable efficiency, but such relatively large flow rates also lead to substantial loss and wasteage of the nebulized drug, due primarily to the fact that the flow rates in such range exceed the patient uptake rate on a continuous basis.

It is possible to reduce carrier gas flow rate below such 6–8 liter per minute range, but at such lower flow rates, nebulization efficiency becomes disproportionately poorer as the flow rate is reduced to levels as low as 4–5 liters per minute, with the result that a carrier gas flow rate of 4 liters per minute is considered a conventional "low flow" regime defining the limits of operability of commercially available liquid nebulizer devices.

Further, even at such "low flow" conditions on the order of 4–5 liters per minute, the tidal volume respiratory gas is substantially larger than lung capacity for neonatal patients and others with reduced lung capacity such as patients who possess only one lung. At low flow rates, on the order of 4–5 liters per minute, the nebulization efficiency becomes unsuitable since the gas flow rate is not adequate to produce a usefully fine particle size distribution of the medicant.

Accordingly, where low flow delivery of medicant materials is required, the only practical device is an ultrasonic nozzle. However, ultrasonic nozzles suffer the deficiencies that they are costly, tend to denature a variety of otherwise useful drugs which in denatured form are non-efficacious, and ultrasonic nozzles tend to have a short operating life, due to nozzle wear and degradation.

It would therefore be highly desirable to provide a liquid nebulizer device which is usefully employed to deliver medicant materials in a carrier gas flow stream at a flow rate substantially below the range of 4–5 liters per minute, which is the practical lower limit with conventional nebulizer apparatus.

Accordingly, it is an object of the present invention to provide such a liquid nebulizer system capable of operating at carrier gas flow rates substantially below the 4–5 liter per minute practical lower limit of currently available commercial nebulizer devices.

It is another object of the present invention to provide a nebulization system of such type which may be used for delivery of liquid as well as solid medicaments.

It is a further object of the present invention to provide a method and apparatus for continuous respiratory delivery by low flow rate gas nebulization of liquid medicaments.

It is still another object of the present invention to provide a method and apparatus for respiratory delivery of low gas flow nebulization of liquid medication which may be used in ventilatory circuits.

It is yet another object of the invention to provide a method and apparatus which overcome the disadvantages associated with currently available respiratory medicant delivery systems.

These and other objects and advantages of the present invention will be more fuly apparent from the ensuing disclosure and appended claims.

SUMMARY OF THE INVENTION

In a broad apparatus aspect, the present invention relates to a nebulizer device, comprising:

(a) a housing defining an interior volume therewithin, including a reservoir portion for holding medicament therein for entrainment into a carrier gas to form a delivery gas mixture comprising nebulized medicament and carrier gas;

(b) a discharge port connected to the housing in flow communication with the interior volume therewithin, for discharging the delivery gas mixture from the housing;

(c) a jet passage member having (i) an inlet portion for introduction of carrier gas thereinto and (ii) a nozzle portion postioned in the interior volume of the housing for discharging carrier gas in jet form in the interior volume, for entrainment of medicament from the reservoir portion of the housing in the carrier gas jet, said nozzle portion comprising a nozzle orifice accomodating carrier gas flow therethrough, wherein the nozzle orifice has an equivalent orifice diameter in the range of from about 0.005 inch to about 0.020 inch.

In the above-described apparatus, the nozzle orifice preferably is in the range of from about 0.007 inch to about 0.018 inch, more preferably from about 0.008 inch to about 0.015 inch, and most preferably from about 0.010 inch to about 0.012 inch.

The nebulizer device in one embodiment particularly suited for nebulization of liquid medicants may further comprise means disposed in the interior volume of the housing for delivering liquid from the reservoir portion of the housing to a discharge locus of the nozzle orifice of the jet passage member, whereby delivered liquid is entrained in carrier gas flowed through the jet passage member when the reservoir portion contains liquid. In a specific embodiment, such means may comprise a nebulization structure mounted in the interior volume of the housing, including: an expansion chamber in flow-receiving communication with the nozzle portion of the jet passage member, such expansion chamber having an orifice therein, in alignment with the orifice of the jet passage member; an impingement baffle presenting an impingement surface in alignment with the orifices of the jet passage member and the expansion chamber; and means for aspiratingly delivering liquid from the reservoir portion of the housing when liquid is contained in the reservoir and carrier gas is flowed in sequence through the orifices of the jet passage member and the expansion chamber at sufficient volumetric flow rate. In such embodiment, the orifice in the expansion chamber has an equivalent orifice diameter in the range of from about 0.025 inch to about 0.060 inch, and preferably from about 0.030 inch to about 0.050 inch.

The nebulizer devide of the invention may further comprise pressurized carrier gas supply means coupled in gas-supplying relationship with the inlet portion of the jet passage member, and/or a breathing circuit coupled with the discharge port for receiving delivery gas mixture and conveying same to a patient interconnected with the breathing circuit.

In one method aspect, the present invention relates to a method of delivering a nebulized medicant to a patient, comprising:

(a) providing a nebulizer apparatus including a breathing circuit coupled to the patient and including a nebulizer device (i) containing the medicant, and (ii) constructed and arranged for producing a pulmonarily effective nebulized medicant in a carrier gas passed through the nebulizer device at a carrier gas flow rate in the range of from about 0.5 to about 3.25 liters per minute;

(b) flowing the carrier gas through the nebulizer device at a flow rate in the range of from about 0.5 to about 3.25 liters per minute, to disperse the medicant into the carrier gas and form said pulmonarily effective nebulized medicant in the carrier gas, as a medicant-/carrier gas mixture; and (c) passing the medicant/carrier gas mixture through the breathing circuit to a pulmonary situs of the patient.

In another method aspect, the present invention relates to a method of delivering a nebulized medicant to a patient, comprising:

(I) providing a nebulizer apparatus including a breathing circuit coupled to the patient and including a nebulizer device, wherein the nebulizer device comprises:

(a) a housing defining an interior volume therewithin, including a reservoir portion for holding medicament therein for entrainment into a carrier gas to form a delivery gas mixture comprising nebulized medicament and carrier gas;

(b) a discharge port connected to the housing in flow communication with the interior volume therewithin, for discharging the delivery gas mixture from the housing;

(c) a jet passage member having (i) an inlet portion for introduction of carrier gas thereinto and (ii) a nozzle portion postioned in the interior volume of the housing for discharging carrier gas in jet form in the interior volume, for entrainment of medicament from the reservoir portion of the housing in the carrier gas jet, such nozzle portion comprising a nozzle orifice accomodating carrier gas flow therethrough, wherein the nozzle orifice has an equivalent orifice diameter in the range of from about 0.005 inch to about 0.020 inch;

(II) disposing a medicant in the reservoir portion of the housing;

(III) flowing the carrier gas through the jet passage member of the nebulizer device at a flow rate in the range of from about 0.5 to about 3.25 liters per minute, to disperse the medicant into the carrier gas and form a pulmonarily effective nebulized medicant in the carrier gas, as a medicant/carrier gas mixture; and (IV) passing the medicant/carrier gas mixture through the breathing circuit to a pulmonary situs of the patient.

In the practice of the method of the present invention, the carrier gas flow rate preferably is in the range of from about 1.0 to about 3.0 liters per minute, and most preferably is in the range of from about 2.2 to about 2.8 liters per minute.

The medicant which is administered to the patient in the practice of the nebulization technology of the present invention may for example comprise a material selected from the group consisting of lung surfactants or precursors thereof, terbutaline, salbutamol, dexamethasone, chromolyn sodium, pentamidine, and bioactive substances encapsulated in a pulmonarily degradeable encapsulant medium.

As used herein, the term "equivalent orifice diameter" refers to the diameter of an orifice having a circular opening which is equivalent in cross-sectional open area (i.e., the open area of the orifice opening perpendicular to the direction of the flow of carrier gas therethrough) to the cross-sectional open area of the actual orifice in the nebulization system of the present invention. This terminology defines the dimensional character of the orifice regardless of the actual shape of the orifice opening, and thus the invention contemplates the employment of orifice openings which are of circular or generally circular opening shape, as well as orifice openings which are of non-circular or irregular opening shape. Of course, when the orifice opening is of circular shape, the equivalent orifice diameter of such opening is identical to its actual diameter. Preferably, the orifice opening is of circular shape, or at least generally circular shape, although as mentioned, other non-circular shapes, e.g., square, ovoid, rectangular, star-shape, cruciform, etc. shapes, may advantageously be employed within the broad practice of the present invention.

As used herein, the terms "medicant" and "medicament" are intended to be broadly construed to include any substances, formulations, compositions, compounds, materials, etc. which are physiologically beneficial.

As used herein, the term "pulmonarily effective" means physiologically beneficial in application to a patient at a pulmonary situs, viz., the lungs and associated inspiratory and expiratory passages and body structures.

BRIEF DESCRIPTION OF THE DRAWINGS

FIG. 1 is a schematic representation of a patient receiving respiratory support and medication via a continuous flow liquid nebulizing device interposed between an endotracheal tube and a ventilator.

FIG. 2 is an exploded perspective view of a nebulizer and a continuous flow supporting system comprising a large medication storage vessel, a rate controllable pump, an influent port accessible nebulizer vial separated from the nebulizer device upper portion, and influent flow regulating and supply devices.

FIG. 3 is an elevational cross-section of the nebulizer device of FIG. 2.

FIG. 4 is an elevational cross-section of a low flow rate jet structure of a type such as may be alternatively employed in the nebulizer device of FIG. 2.

FIG. 5 is a schematic representation of a patient receiving respiratory support and medication via a powder nebulizing device interposed between an endotracheal tube and a ventilator.

FIG. 6 is an elevational cross-section of the powder nebulizer device of FIG. 5.

DETAILED DESCRIPTION OF THE INVENTION, AND PREFERRED EMBODIMENTS THEREOF

In this description, the term "proximal" is used to indicate the segment of the device normally closest to the patient when it is being used. The term "distal" refers to the other end. Herein the term "nebulizer device" is defined to be a nebulizing unit or instrument used to aerosolize fluid or disperse particulate solid material, e.g., powder, for delivery to a patient. The term "nebulizer vial" is sometimes used herein to denote the portion of a nebulizing device which comprises a container providing a reservoir for fluid or particulate solid material to be nebulized. The term "nebulizer" is sometimes used herein to denote the non-nebulizer-vial portion of the nebulizing device which comprises at least a portion of the nebulizing mechanism. Reference is now made to the embodiments illustrated in FIGS. 1-3 wherein like numerals are used to designate like parts throughout.

Figure 1:
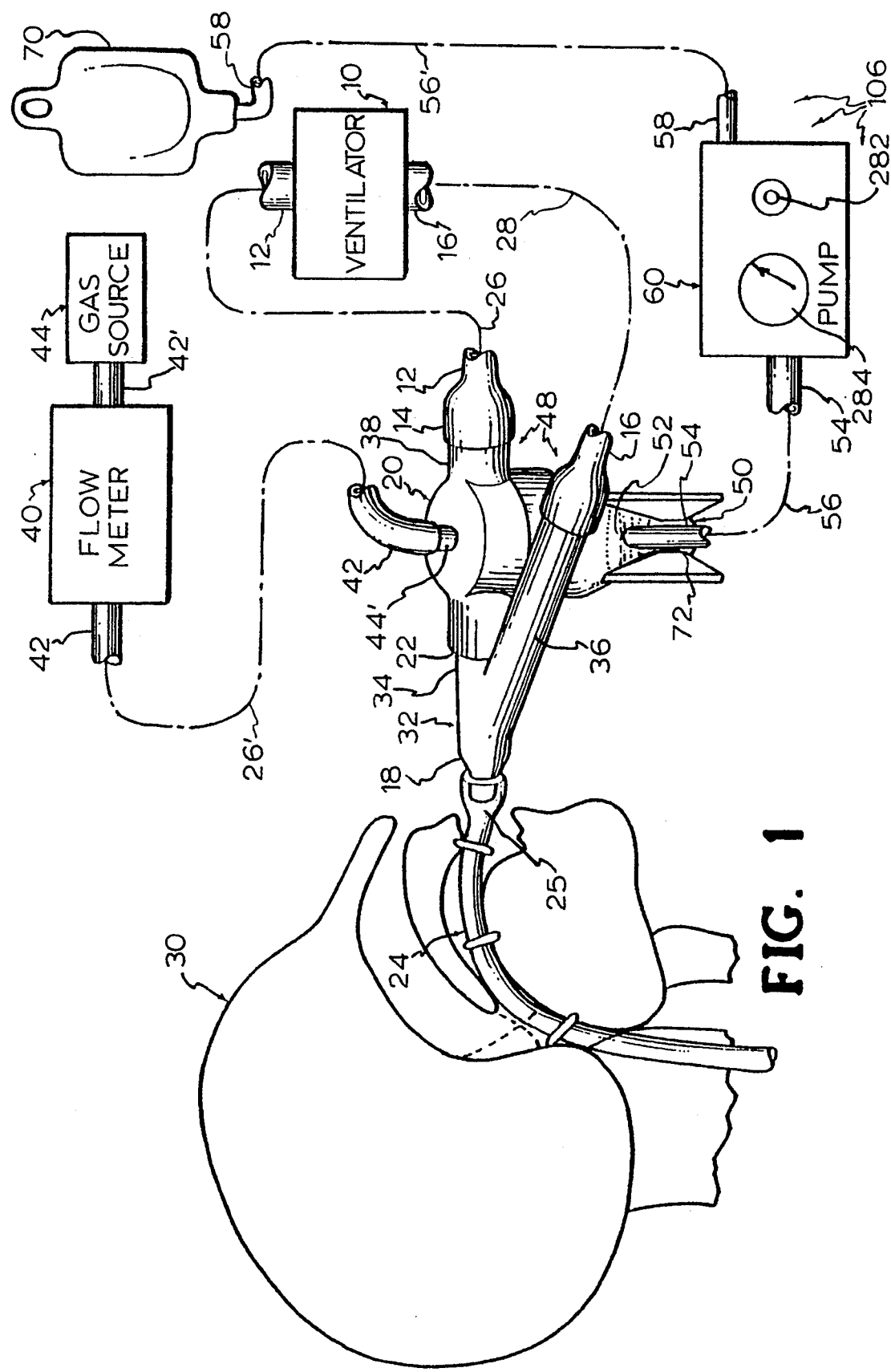
Figure 2:
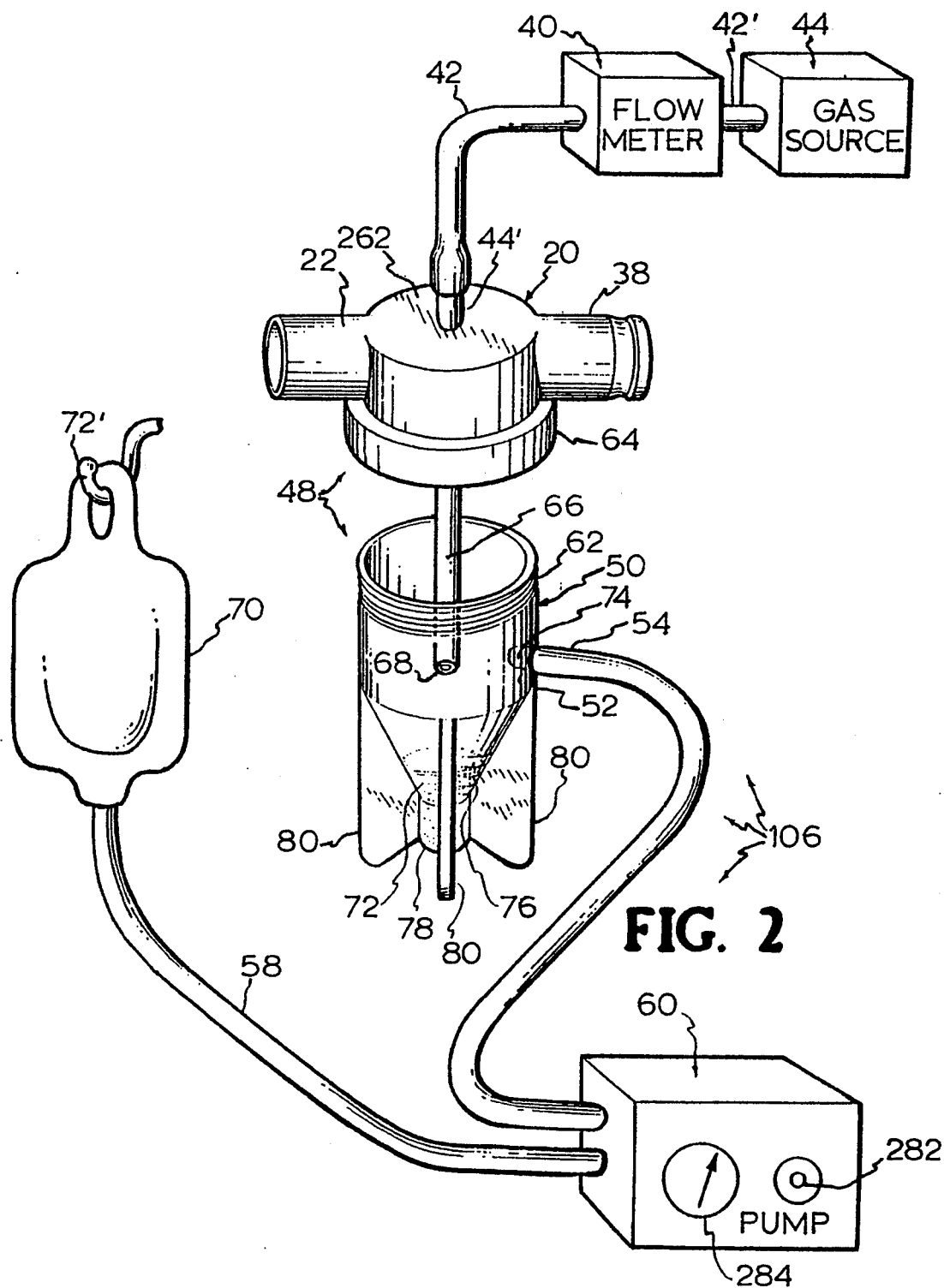

As seen in FIG. 1, a patient 30, undergoing respiratory therapy, is fitted with an endotracheal tube 24. The proximal trunk end 18 of a "Y"-shaped connector 32 is insertably connected to a distal end 25 of endotracheal tube 24. One bifurcated distal end 34 of "Y"-shaped connector 32, is insertably connected to a proximal port 22 of a nebulizer 20 which is part of a nebulizing device 48. Nebulizer 20 is disposed between distal end 34 of "Y"-shaped connector 32 and a proximal end 14 of a respiratory gas delivery tube 12. Thereat a distal part 38 of nebulizer 20 is insertably connected to gas delivery tube 12. Gas delivery tube 12 provides the distal portion of inhalation respiratory pathway 26 and connects to the output inhalation gas of a ventilator 10. Ventilator 10 therapy supplies periodic, breath-sustaining pulses of pressurized gas through tube 12, nebulizer device 48, and "Y"-shaped connector 32 into endotracheal tube 24 and to patient 30.

The other distal end 36 of "Y"-shaped connector 32 comprises a proximal portion of an exhalation respiratory pathway 28 which further comprises tube 16 which returns exhalation flow to ventilator 10. Many different ventilators are known and available in the art. Generally, ventilators which are conventionally used with nebulizers may be used with the invention.

Nebulizer 20 receives a supply of nebulizing gas from a flow meter 40 along a fluid pathway 26' which passes through a tube 42 interposed and connected between flow meter 40 and a top nebulizer inflow connecting tube 44'. Flow meter 40 receives a pressurized gas from a gas source 44 through a connecting tube 42'. Gas pressure from gas source 44 is sufficient to provide the volumetric flow for which flow meter 40 is preset. Gas source 44 may comprise pressurized oxygen or other breathable gas from a hospital pressurized $O_2$ delivery system, from a tank of compressed oxygen, a blender, directly from ventilator 10, or from other sources of pressurized gases conventionally used in respiratory therapy. Flow meters are well known and widely used in the art. Such flow meters may comprise macro and vernier adjustable controls for very accurate and precise gas flow settings. Although $O_2$ is preferred for some selected medicants, source 44 may supply oxygen blended with other gases.

Nebulizing device 48 comprises nebulizer 20 which functions in combination with an attached nebulizer vial 50. Nebulizing device 48 nebulizes or aerosolizes fluids contained in reservoir 72 in nebulizer vial 50, thereby producing a mist which is carried to patient 30 by influent flow of gas from ventilator 10 through pathway 26 and by nebulizing gas received from gas source 44. Delivery of nebulized fluid to patient 30 is therefore dependent upon the availability of fluid resident in the reservoir 72 at any given moment.

In a currently preferred embodiment shown in FIGS. 1 and 2, a continuous flow system 106 provides substantially continuous delivery of fluid to nebulizer vial 50 to maintain the volume of liquid at an adequate and essentially unchanging level in reservoir 72. Continuous flow system 106 comprises (i) nebulizer vial 50, (ii) at least one influent access port 52 to nebulizer vial 50, (iii) connecting tubing 54 interposed between a pump 60 and connected at influent access port 52, (iv) the pump 60, (v) additional tubing 58 providing a medicant pathway 56′ interposed between and connected pump 60 and a large medicant supply vessel 70, and (vi) the large medicant supply vessel 70. Continuous flow system 106 maintains a constant volume of liquid in nebulizer vial 50, in which continuation of such constant volume condition is not dependent upon the initial contents of reservoir 72 at the time nebulizer vial 50 is joined to nebulizer 20, but upon the larger volume available in large medicant supply vessel 70. Such supply vessels may be IV bags, bottles or other nebulizing medication and reagent containing vessels from which therapeutic liquids are drawn.

As seen in FIG. 2, nebulizing device 48 comprises nebulizer vial 50 which releasibly and sealably attaches to nebulizer 20. Such attachment may be by a male threaded member 62 of nebulizer vial 50 insertably joined into a female threaded member 64 of nebulizer 20. When nebulizer 20 is so disposed and connected to nebulizer vial 50, an end 68 of an aspirator tube 66 is disposed below the surface of a reservoir 72 in the bottom of nebulizer vial 50 as best seen in FIG. 3.

Nebulizer 20 may be a general construction similar to commercially available nebulizer devices generally used for administration of aerosolized fluids but featuring a jet passage member having (i) an inlet portion for introduction of carrier gas thereinto and (ii) a nozzle portion positioned in the interior volume of the nebulizer housing for discharging carrier gas in jet form in the interior volume, for entrainment of medicament from the reservoir portion of the housing in the carrier gas jet, with the nozzle portion comprising a nozzle orifice accommodating carrier gas flow therethrough, wherein the nozzle orifice has an equivalent orifice diameter in the range of from about 0.005 inch to about 0.020 inch, preferably from about 0.007 inch to about 0.018 inch, more preferably from about 0.008 inch to about 0.015 inch, and most preferably from about 0.010 inch to about 0.012 inch. Nebulizer vial 50 may suitably comprise a container made to releasibly but sealably attach to commercially available nebulizer 20 and, in combination with a gravitational or mechanical pump and a large supply vessel, provide a continuously filled reservoir 72 from which medicants are aspirated via aspirator tube 66 into nebulizer 20 and aerosolized. Alternatively the nebulizer vial may be of a conventional type, uconnected to any external liquid supply vessel, for delivery of a unitary dose of medicant from the reservoir portion 72 of the nebulizer housing.

FIG. 3 provides a sectional view of nebulizing device 48, comprising nebulizer 20 threadably interconnected to nebulizer vial 50. The following description of nebulizer 20 is provided for a general understanding of the interaction between nebulizer 20 and nebulizer vial 50.

Figure 3:
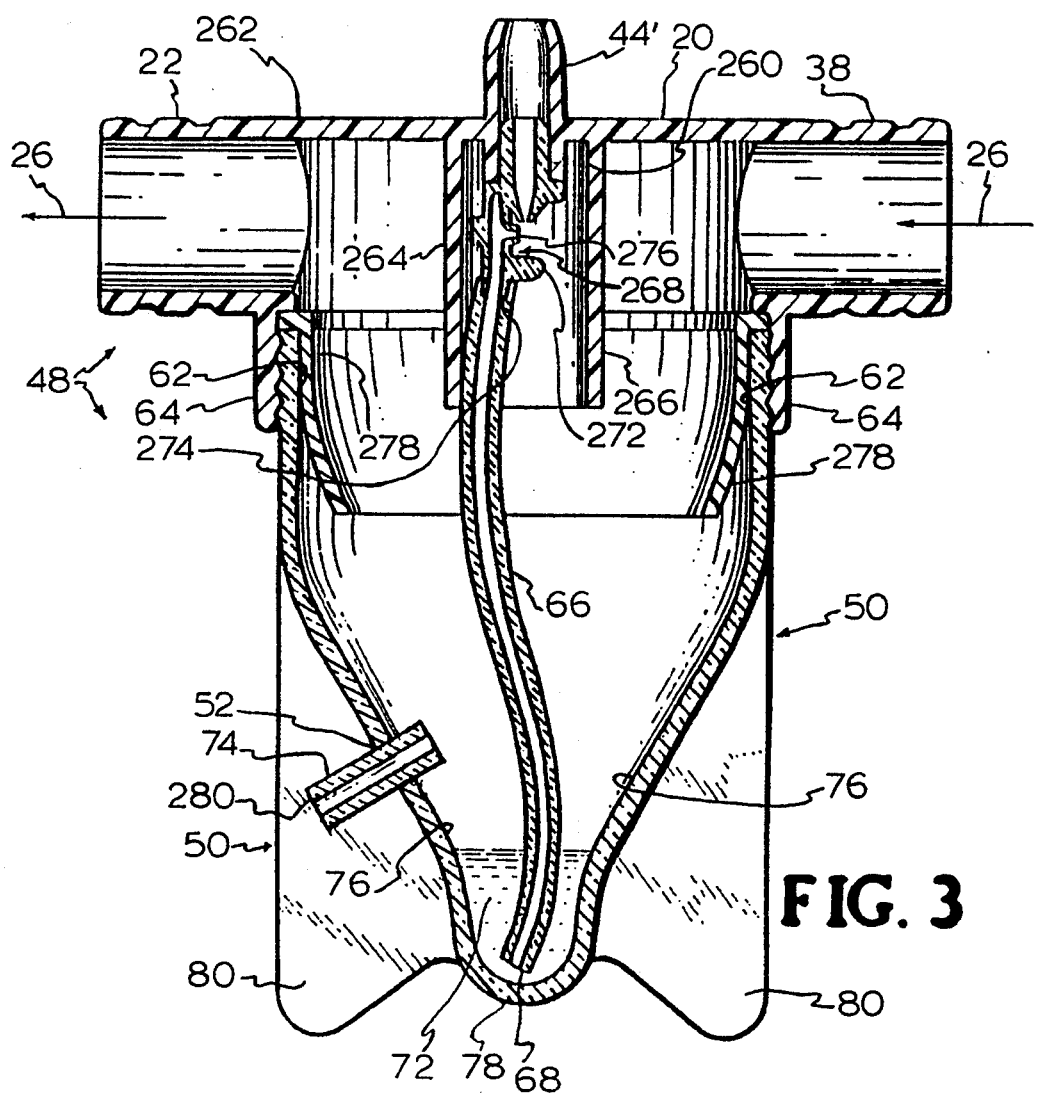

Nebulizer 20, as seen in FIG. 3, comprises a housing 262 which comprises a top nebulizer inflow connecting tube 44', a jet passage member 260, with nozzle orifice 203 in the lower nozzle portion thereof, a baffle assembly 268, and aspirator tube 66. Baffle assembly 268 further comprises an aspirator tube connecting orifice 274, a liquid effluent orifice 276, and an impingement baffle 272 in the form of a baffle plate presenting an impingement surface to gas exiting nozzle orifice 203 and liquid entrained in the gas from liquid effluent orifice 276. Pressurized gas which provides the nebulizing high velocity stream for nebulization is provided through top nebulizer inflow connecting tube 44'. The high velocity stream is produced by jet passage member 260 in the direction of impingement baffle 272. As the high velocity stream passes by liquid effluent orifice 276 a resulting below ambient pressure at orifice 276 draws liquid therethrough which is carried by the high velocity carrier gas stream to impact against the impingement surface of impingement baffle 272 to thereby produce a mist.

Housing 262 further comprises a pair of baffles 264 and 266 which lie in inhalation pathway 26 and shield the space where nebulization occurs. A hollow frustoconical baffle 278 is disposed in the medial space between inhalation pathway 26 and the extension of baffles 264 and 266 to limit air flow into nebulizer vial 50 and aid in entraining mist into inhalation pathway 26. While this description of an illustrative nebulizer embodiment is for a single connecting tube 44', nozzle 260 and associated parts, the number of inflow connecting tubes, nozzles, and associated nebulizer parts may vary in the nebulizer as is well known in the art.

Nebulizer vial 50 is suitably made from synthetic resinous material and preferably is transparent for easy monitoring by a respiratory technician or other patient attendant. The materials of construction of nebulizer vials are well known in the art. They are usually of chemically-inert thermoplastic such as polyolefins or polyvinyl chlorides. Their selection and fabrication are well within the skill of the art.

As seen in FIGS. 2 and 3, nebulizer vial 50 comprises a port 52 and a therethrough inserted feedthrough 74. Also as seen in combination in FIGS. 2 and 3, port 52 may be located at different sites in nebulizer vial 50 as required to meet tubing placement and other physical fluid delivery restrictions. As seen in FIG. 2, tube 54 is engaged about feedthrough 74 to be releasibly but snugly affixed thereat in pressure-sealed relation. Feedthrough 74 comprises a through hole 280, as seen in FIG. 3, through which fluid received under pressure from pump 60 flows into nebulizer vial 50. The bottom of nebulizer vial 50 comprises an inverted conically shaped part 76. Apex 78 of inverted conically shaped part 76 provides a low point for fluid contained in reservoir 72 where apirating tube 66 end 68 is normally disposed when nebulizer 20 is affixed to nebulizer vial 50. A plurality of legs 80 provide a level support when nebulizer vial 50 is disposed on a horizontal surface to maintain fluid at the bottom of inverted conically shaped part 76.

Referring again to FIG. 2, large supply vessel 70, seen to be in the form of a plastic container bag, is disposed on a hook 72', such as an IV bag is hung. Tube 58 provides the fluid pathway to pump 60. Pump 60 comprises rate control dial 282 and flow rate display 284 which provide for manual flow rate adjustment. Thereby, the flow rate of pump 60 is set to provide a rate of flow of liquid into nebulizer vial 50 which is substantially equal to the rate of loss of liquid from the reservoir 72 through aerosolization. Such a flow rate for pump 60 is derived from a nomogram which comprises the variables of gas flow through flow meter 40 and through ventilator 10. A different homogram is generated for each combination of nebulizer 20, flow meter 40, and ventilator 10. Derivation of such nomograms is well within the skill of the art. As disclosed above, pump 60 is a variable flow controlling pump which provides and maintains an accurate and precise flow rate. Pump 60 may be a syringe infusion pump, model number 2001, available from Medfusion, a Medox, Inc. Company, 3450 River Green Court, Duluth, Ga. 30136.

FIG. 4 is a cross-sectional elevation view of a nebulization structure 300 which is mountable in the interior volume of a nebulizer housing, as for example a nebulizer housing of the type illustratively shown and described with respect to FIGS. 1-3 hereof.

Nebulization structure 300 includes a jet passage member 302 having an inlet portion 304 for introduction of carrier gas thereinto, such carrier gas being introduced from suitable conduit or flow circuit means (not shown) to effect flow of carrier gas into the inlet portion 304 of jet passage member 302 in the direction indicated by arrow A in FIG. 4.

Jet passage member 302 further includes a nozzle portion 306, which is positioned in the interior volume of the nebulizer housing, for discharging carrier gas in jet form in the interior volume, through nozzle orifice 308. The nozzle orifice has an equivalent orifice diameter in the range of from about 0.05 inch to about 0.020 inch, and preferably is at least generally circular in cross-sectional shape, transverse to the flow direction indicated by arrow A.

By this arrangement, carrier gas passing through the jet passage member 302 flows through the nozzle orifice 308 in the direction indicated by arrow B, with the carrier gas flow rate suitably being on the order of from about 1.75 to about 3.25 liters per minute.

In this embodiment of FIG. 4, the nebulization structure 300 further comprises an expansion chamber 310 in flow-receiving communication with the nozzle portion 306 of the jet passage member. The expansion 310 defines an expansion volume 312 therewithin, and the expansion chamber includes an orifice 314 through which the carrier gas is flowed in the direction indicated by arrow C subsequent to entrainment in such carrier gas of liquid to be nebulized, which enters the expansion volume 312 in the direction indicated by arrow D, from extension tube 316 of the expansion chamber. Expansion tube 316 has a lower open end 318 as shown, and the tube is journaled or otherwise secured in closed flow relationship to aspiration tube 320 having an interior flow passage 322 and a lower open end 324 into which liquid is aspiratingly drawn in the direction indicated by arrow E.

Secured to the aspiration tube 320, as shown, by means of arm 326 is an impingement member 328 presenting an impingement surface on its upper portion onto which the delivery mixture comprising carrier gas and entrained liquid is impinged, for dispersion in the directions indicated by arrows F in FIG. 4.

The impingement member 328 may, as shown, feature a convex impingement surface, whereby dispersion in a wide variety of directions in the interior volume, is achieved.

In use, the nebulization structure 300 is disposed so that the lower open end 324 of aspiration tube 320 is disposed in a pool or body of liquid medicant in the lower reservoir portion of the nebulizer housing. The flow of carrier gas in the direction indicated by sequential arrows A, B, and C causes a reduced gas pressure in the expansion chamber 312 which effects aspiration of liquid through aspiration tube 320 and extension tube 316 to the locus of the expansion chamber 310 interior volume 312 in proximity to nozzle orifice 308. By this arrangement, a highly efficient dispersion of liquid into the gas is achieved, and the droplet size distribution is extremely favorable for highly efficient nebulization, due to the fineness of the mist liquid particles thereby obtained.

Nozzle orifice 308 may suitably have an equivalent orifice diameter in the range of from about 0.005 inch to about 0.020 inch, preferably in the range of from about 0.007 to about 0.018 inch, more preferably from about 0.008 inch to about 0.015 inch, and most preferably from about 0.010 inch to about 0.012 inch.

At equivalent orifice diameter values below about 0.005 inch, the orifice becomes disporportionately more difficult to reliably manufacture and fabricate. Above about 0.020 inch, the velocity of carrier gas flow achievable by the jet passage member becomes unsuitably low to accommodate the low gas flow rate nebulization conditions desired in the practice of the invention. The further preferred, more preferred, and most preferred ranges represent further balances of these corresponding considerations associated with the end points of the broad range of equivalent orifice diameter values.

Similar considerations dictate the range of permissible sizes potentially employable for the expansion chamber orifice 31 4, which suitably has an equivalent orifice diameter in the range of from about 0.025 inch to about 0.060 inch, and more preferably from about 0.30 inch to about 0.050 inch.

Figure 5:
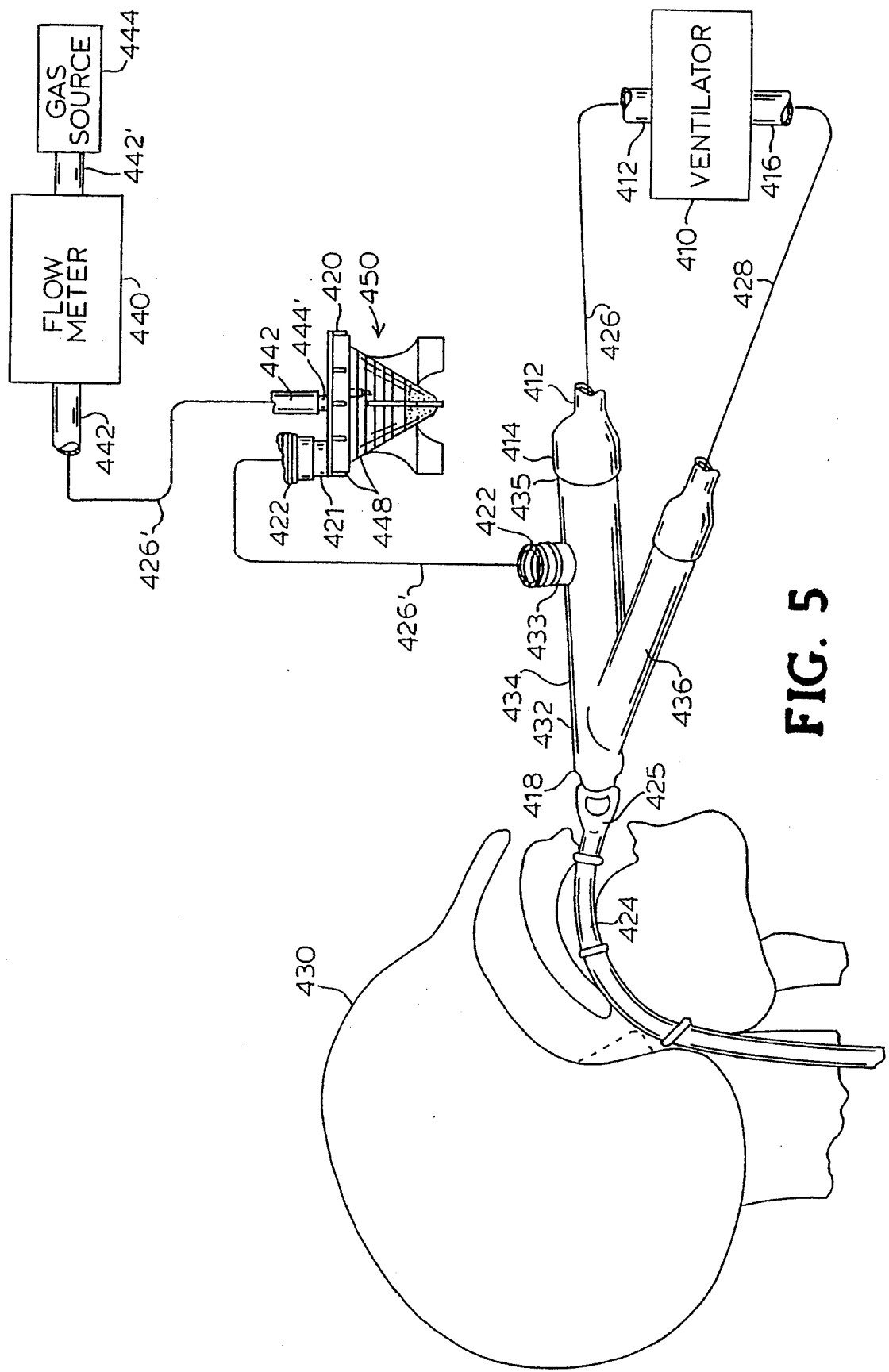
Figure 6:
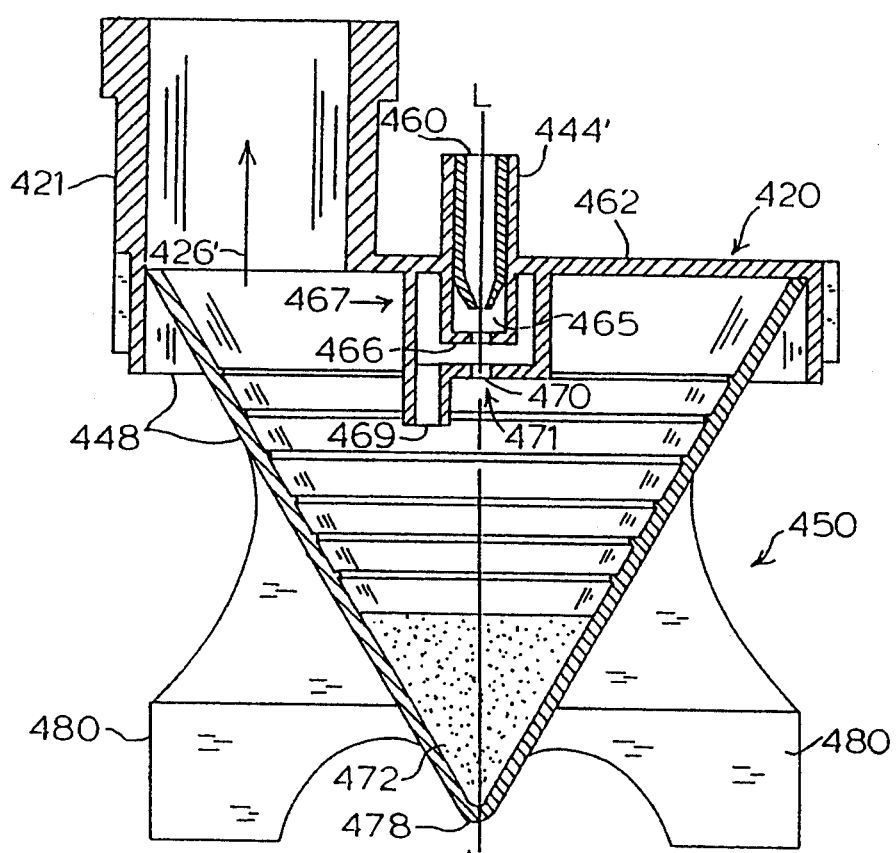
Figure 4:
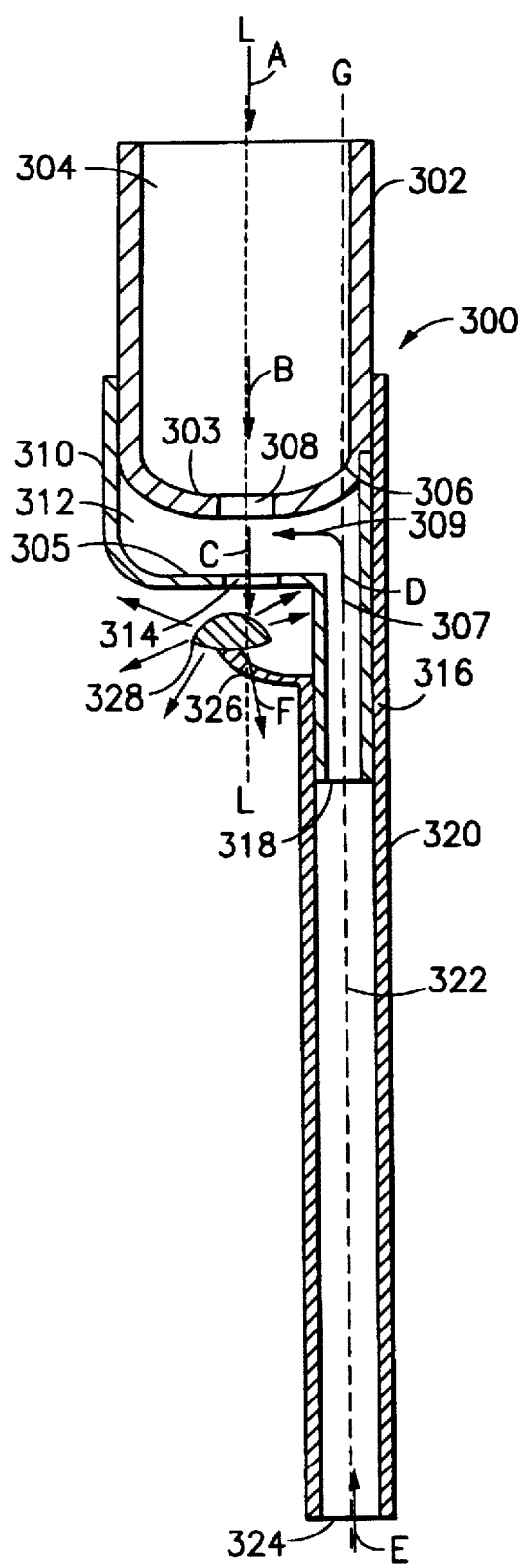

Corresponding operational considerations govern the gas flow rate past through the jet passage member of the nebulizer device. In accordance with the low flow rate nebulization method of the present invention, the carrier gas flow rate through the jet passage member is advantageously in the range of from about 0.5 to about 3.25 liters per minute, to disperse the medicant into the carrier gas and form a pulmonarily effective nebulized medicant in the carrier gas, as a medicant/carrier gas mixture. At flow rate values below about 0.5 liters per minute, the volumetric flow rate of carrier gas tends to become insufficient to achieve good dispersion of the medicant in the flowing gas stream. At volumetric flow rate values above about 3.25 liters per minute, the small-size orifice dimensions employed in the practice of the invention tend to produce a back pressure which renders it disporportionately more difficult to achieve a reliable coupling and seal between the inlet portion of the jet passage member and the associated carrier gas flow means. Preferably, the volumetric carrier gas flow rate is in the range of from about 1.0 to about 3.0 liters per minute, and most preferably is in the range of from about 2.2 to about 2.8 liters per minute, based on corresponding considerations, as regards the end point values of the preferred and most preferred ranges, corresponding to the reasons set out above in the respect of the end points of the broad volumetric flow rate range of from about 0.5 to about 3.25 liters per minute. The nebulizer device and nebulization method of the present invention are usefully employed with any of a wide variety of nebulizable materials, including liquid and solid medicants, liquid medicants being advantageously practiced with liquid nebulizer devices in accordance with the present invention, as illustratively embodied in the device shown and described with reference to FIGS. 1–3 hereof, and the nebulization structure alternatively described in connection with FIG. 4 hereof; particulate solid, e.g., powdered, medicants may usefully be administered with powder nebulizer means as more fully shown and described in our prior copending U.S. patent application Ser. No. 07/846,784 filed Mar. 4, 1992, the disclosure of which hereby is incorporated herein by reference. An illustrative powder nebulizer potentially useful in the broad practice of the present invention is illustratively described hereinafter with reference to FIGS. 5 and 6 herein.

Illustrative of medicants which may be administered utilizing the nebulization technology of the present invention are materials such as lung surfactants or precursors thereof (precursors being materials or substances which are converted in situ in the pulmonary locus to surfactant material), terbutaline, salbutamol, dexamethasone, chromolyn sodium and pentamidine, and bioactive substances encapsulated in a pulmonarily degradable encapsulant medium (i.e., a medium in which the bioactive substance is encapsulated and which is degradable in the pulmonary locus to release the bioactive substance). The liquid nebulizer apparatus in accordance with the present invention is particularly usefully employed for administration of lung surfactants, such as NEOSURF® (Burroughs Wellcome Company, Research Triangle Park, N.C.) and pentamidine, which is usefully employed in the treatment of pneumocystis infections accompanying HIV infection, and development of ARC and AIDS.

In application to particulate solids nebulization, the present invention contemplates a method of forming a solid particle dispersion with the use of a carrier gas at the low volumetric flow rate values discussed hereinabove, and with a suitably configured nebulizer apparatus, featuring a jet passage member having the dimensional characteristics described hereinabove.

In the practice of nebulizing particulate solid medicants in the practice of the present invention, the nebulizer housing includes a reservoir portion for the particulate solid medicant, which preferably is generally conical-shaped or funicular in shape, for containing the particulate solid to be dispersed. A jet of carrier gas is directed downwardly through the jet passage member to the lower extremity of such generally conical-shaped or funicular-shaped receptacle to entrain particles of the particulate solid in the carrier gas, to form a solids dispersion in the carrier gas which then is discharged from the nebulizer device to suitable breathing circuitry means.

In a preferred particulate solid medicant nebulization system, the gas stream directed at the particulate solid is passed through the nozzle orifice of the jet passage member, then expanded and passed through a second orifice of the expansion chamber, with an entrainment structure channeling gas from the receptacle to the jet structure, to increase total gas flow and assist in the production of a gas jet flow stream of desired velocity and pressure characteristics. The entrainment structure may comprise a chamber defining a plenum, with an entrainment port communicating in gas flow relationship with the interior volume of the housing, and with an outlet port communicating with the second orifice to cooperatively form a jet structure therewith, as described in the aforementioned prior copending application Ser. No. 07/846,784 now U.S. Pat. No. 5,186,166.

Referring now to the solids nebulization system shown in FIG. 5, a patient 430, undergoing respiratory therapy, is fitted with an endotracheal tube 424. The proximal trunk end 418 of a "Y"-shaped connector 432 is insertably connected to a distal end 425 of endotracheal tube 424. Nebulizing device 448 is connected to arm 434 of "Y"-shaped connector 423 via tube 422 which is interposed and connected between exit port 421 of nebulizer device 448 and arm 434 of the "Y"-shaped connector 432 at port 433. A distal end 435 of arm 434 is insertably connected to a proximal end 414 of gas delivery tube 412. Gas delivery tube 412 provides the proximal portion of inhalation respiratory pathway 426 and connects to the output inhalation gas of a ventilator 410. Ventilator 410 supplies periodic, breath-sustaining pulses of pressurized gas through tube 412 and through arm 434 of "Y"-shaped connector 432 into endotracheal tube 424 and to patient 430.

The other distal end 436 of "Y"-shaped connector 432 comprises a proximal portion of an exhalation respiratory pathway 428 which further comprises tube 416 which returns exhalation flow to ventilator 410. Many different ventilators are known and available in the art. Generally, ventilators which are conventionally used with nebulizers may be used with the present invention.

Nebulizer device 448 receives a supply of nebulizing gas from a flow meter 440 along a fluid pathway 426' which passes through a tube 442 interposed and connected between flow meter 440 and a top nebulizer inflow connecting tube 444'. Flow meter 440 receives a pressurized gas from a gas source 444 through a connecting tube 442'. Gas pressure from gas source 444 is sufficient to provide the volumetric flow for which flow meter 440 is preset. Gas source 444 may comprise pressurized oxygen or other breathable gas from the hospital pressurized oxygen delivery system, from a tank of compressed oxygen, a blender, directly from ventilator 410 or from other sources of pressurized gases used in respiratory therapy. Flow meters are well known and widely used in the art. Such flow meters may comprise macro and vernier adjustable controls for very accurate and precise gas flow setting. Although oxygen is preferred for some selected medicants, gas source 444 may supply oxygen blended with other gases.

Nebulizing device 448 comprises nebulizer upper portion 420 and a nebulizer receptacle 450. Nebulizing device 448 nebulizes or aerosolizes powdered medication contained in nebulizer receptacle 450 thereby producing a mist (particulate solids-in-gas dispersion) which is carried to patient 430 by influent flow of gas from ventilator 410 through pathway 426 and by nebulizing gas received from gas source 444.

The nebulizing device 448 comprises nebulizer receptacle 450 which is attached to nebulizer upper portion 420. In a specific embodiment, the top of the nebulizer receptacle 450 is 1.5 inches in diameter, the bottom is 0.25 inches in diameter, and the nebulizer receptacle 450 measures 1.5 inches from top to bottom. As shown in FIG. 6, an end of nozzle 466 is disposed above the surface of a reservoir 472 in the bottom of the nebulizer receptacle 450.

While specific dimensions and tolerances are ilustratively set forth herein in respect of the preferred embodiments of the invention, it will be appreciated that the specific size, design, dimensions, and tolerances, may be varied widely within the broad scope of the present invention, with the choice of a specific set of such design parameters being dependent on the particular end use application contemplated in a given instance. The present invention may be embodied in the various embodiments illustrated in our prior co-pending U.S. patent application Ser. No. 07/729,518, filed Jul. 12, 1991, the disclosure of which is hereby incorporated herein by reference.

FIG. 6 provides a sectional view of nebulizing device 448 of FIG. 5, comprising nebulizer upper portion 420 and nebulizer receptacle 450.

The nebulizer upper portion 420, as seen in FIG. 6, comprises a housing 362 which includes a nebulizer inflow connector tube 444', a first nozzle 360, and a second nozzle 466. Pressurized gas is provided through nebulizer inflow connecting tube 444'. The high velocity stream of gas for nebulization is produced by nozzle 360 and nozzle 466. The pressurized gas is discharged from the second nozzle 466. The pressurized gas is discharged from the first nozzle 360 into the receiving volume 465 of the second nozzle 466, thereby undergoing expansion, following which the gas is discharged into entrainment assembly 467. As the high velocity gas stream passes through entrainment assembly 467, a resulting below ambient pressure within entrainment assembly 467, creates a sufficient pressure differential between entrainment port 469 and nebulizer receptacle 450 to draw gas from nebulizer receptacle 450 through entrainment port 469 and into entrainment assembly 467 where the entrained gas is added to the high velocity gas stream being directed toward reservoir 472. The resultingly augmented gas stream exits entrainment assembly 467 through outlet port 470. The high velocity gas stream thus discharged from jet structure 471 engages the powdered medication in the lower portion of nebulizer receptacle 450, which is of progressively decreasing transverse cross-section. As a result, there is achieved a high extent of solids entrainment in the gas stream, as discharged into inhalation pathway 426' via exit 421.

The present invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A small volume nebulizer device, comprising:

(a) a housing defining a nebulizer receptacle having an interior volume therewithin, including a reservoir portion for holding medicament therein for entrainment into a carrier gas to form a delivery gas mixture comprising nebulized medicament and carrier gas, said nebulizer receptacle having a size defining said nebulizer device as a small volume nebulizer device;

(b) a discharge port connected to the housing in flow communication with the interior volume therein, for discharging the delivery gas mixture from the housing;

(c) means for increasing delivery of pulmonarily effective aerosol particles at low flow rates through said nebulizer receptacle, comprising:
  a jet passage member having (i) an inlet means for introduction of carrier gas thereinto and (ii) a nozzle means positioned in the interior volume of the housing for discharging carrier gas in jet form into the interior volume of said nebulizer receptacle for entrainment of medicament from the reservoir portion of the housing in the carrier gas jet, said nozzle portion comprising a nozzle orifice accomodating carrier gas flow therethrough, wherein the nozzle orifice has an equivalent orifice diameter in the range of from about 0.005 inch to about 0.015 inch;
  an impingement baffle presenting an impingement surface in alignment with the orifice of the jet passage member; and pressurized carrier gas supply means coupled in gas-supplying relationship with the inlet portion of the jet passage member, for supplying pressurized carrier gas at a flow rate of from about 0.5 to 2.8 liters per minute.

2. A device according to claim 1, wherein the equivalent orifice diameter is in the range of from 0.008 inch to 0.015 inch.

3. A device according to claim 1, wherein the equivalent orifice diameter is in the range of from 0.010 inch to 0.012 inch.

4. A device according to claim 1, further comprising a nebulization structure mounted in the interior volume of the housing, including: an expansion chamber in flow receiving communication with the nozzle portion of the jet passage member, said expansion chamber having an orifice therein, in alignment with the orifice of the jet passage member; said impingement baffle presenting an impingement surface in alignment with the orifices of both the jet passage member and the expansion chamber; and means for aspiratingly delivering liquid from the reservoir portion of the housing when liquid is contained in the reservoir and carrier gas is flowed in sequence through the orifices of the jet passage member and the expansion chamber at sufficient volumetric flow rate.

5. A device according to claim 4, wherein the orifice in the expansion chamber has an equivalent orifice diameter in the range of from 0.025 inch to 0.060 inch.

6. A device according to claim 4, wherein the orifice in the expansion chamber has an equivalent orifice diameter in the range of from 0.030 inch to 0.050 inch.

7. A device according to claim 1, further comprising a breathing circuit coupled with the discharge port for receiving delivery gas mixture and conveying same to a patient interconnected with the breathing circuit.

8. A device according to claim 1, further comprising means disposed in the interior volume of the housing for delivering liquid from the reservoir portion of the housing to a discharge locus of the nozzle orifice of the jet passage member, whereby delivered liquid is entrained in carrier gas flowed through the jet passage member when the reservoir portion contains liquid.

9. A method of delivering a nebulized medicament to a patient, and increasing delivery of pulmonarily effective aerosol particles at low flow rates comprising the steps of:

(I) providing a nebulizer apparatus including a breathing circuit coupled to the patient and including a small volume nebulizer device, wherein the small volume nebulizer device comprises:
  (a) a housing defining a nebulizer receptacle having an interior volume therewithin, including a reservoir portion for holding medicament therein for entrainment into a carrier gas to form a delivery gas mixture comprising nebulized medicament and carrier gas said nebulizer receptacle having a size defining said nebulizer device as a small volume nebulizer device;
  (b) a discharge port connected to the housing in flow communication with the interior volume therewith in, for discharging the delivery gas mixture from the housing;
  (c) means for increasing delivery of pulmonarily effective aerosol particles at low flow rates through said nebulizer receptacle, comprising:
    a jet passage member having (i) an inlet means for introduction of carrier gas thereinto and (ii) a nozzle means positioned in the interior volume of the housing for discharging carrier gas in jet form into the interior volume of said nebulizer receptacle, for entrainment of medicament from the reservoir portion of the housing in the carrier gas jet, said nozzle portion comprising a nozzle orifice comprising a nozzle orifice accomodating carrier gas flow therethrough, wherein the nozzle orifice has an equivalent orifice diameter in the range of from about 0.005 inch to about 0.015 inch; and
    an impingement baffle presenting an impingement surface in alignment with the orifice of the jet passage member;

(II) disposing a medicament in the reservoir portion of the housing;

(III) flowing the carrier gas through the jet passage member of the jet nebulizer device and nebulizer receptacle at a flow rate in the range of from about 0.5 to 2.8 liters per minute, to disperse the medicament into the carrier gas and form a pulmonarily effective nebulized medicament in the carrier gas, as a medicant/carrier gas mixture; and (IV) passing the medicament/carrier gas mixture through the breathing circuit to a pulmonary situs of the patient.

10. A method according to claim 9, comprising flowing the carrier gas flow rate in range of from 1.0 to 2.8 liters per minute.

11. A method according to claim 9, comprising flowing the carrier gas at a flow rate in the range of from 2.2 to 2.8 liters per minute.

12. A method according to claim 9, wherein the medicant comprises a material selected from the group consisting of lung surfactants or precursors thereof, terbutaline, salbutamol, dexamethasone, chromolyn sodium, pentamidine, and bioactive substances encapsulated in a pulmonarily degradeable encapsulant medium.

13. A method according to claim 9, wherein the medicant comprises a material selected from the group consisting of lung surfactant and pentamidine.

14. A method according to claim 9, comprising providing the equivalent orifice diameter in the range of from 0.007 inch to 0.018 inch.

* * * * *

REEXAMINATION CERTIFICATE (3648th)
United States Patent [19]
Riggs et al.

[11] B1 5,355,872
[45] Certificate Issued  Oct. 20, 1998

[54] LOW FLOW RATE NEBULIZER APPARATUS AND METHOD OF NEBULIZATION

[76] Inventors: John H. Riggs, 201-F Foliage Cir., Cary, N.C. 27511; Barry O. Mangum, P.O. Box 20554, Raleigh, N.C. 27619

Reexamination Request:
No. 90/003,943, Aug. 23, 1995

Reexamination Certificate for:
Patent No.: 5,355,872
Issued: Oct. 18, 1994
Appl. No.: 927,834
Filed: Aug. 10, 1992

Related U.S. Application Data

[63] Continuation-in-part of Ser. No. 846,784, Mar. 4, 1992, Pat. No. 5,186,166.
[51] Int. Cl.$^6$ .................. A61M 11/00; A61M 16/10; B05B 7/14; B05B 1/26
[52] U.S. Cl. .................. 128/200.21; 128/203.12; 128/200.18; 128/203.15; 239/338
[58] Field of Search .................. 128/200.21, 203.12, 128/200.18, 203.15; 239/338

[56] References Cited

U.S. PATENT DOCUMENTS

| | | |
|---|---|---|
| 3,658,059 | 4/1972 | Steil. |
| 3,664,337 | 5/1972 | Lindsey et al.. |
| 3,744,722 | 7/1973 | Burns. |
| 3,762,409 | 10/1973 | Lester. |

OTHER PUBLICATIONS

B.M. Wright, A New Nebuliser, The Lancet, vol. 5, pp. 24–25, Jul. 1958.

T. T. Mercer et al., Operating Characteristics of the Lauterbach and Dautrebande Aerosol Generators, LF–6, Technical Progress Report to the Division of Biology and Medicine of the U.S. Atomic Energy Commission, Contact No. AT(29–2)–1013, Feb. 1963.

T. T. Mercer et al., Operating Characteristics of Some Compressed Air Nebulizers, American Industrial Hygiene Association Journal, vol. 29, pp. 66–78, Jan. 1968.

O. G. Raabe, Generation and Characterization of Aerosols, Inhalation Carcinogenesis, CONF–691001, Proceedings of a Biology Division, Oak Ridge National Laboratory Conference, pp. 123–172, U.S. Department of Commerce, 1970.

O. G. Raabe, The Generation of Aerosols of Fine Particles, Fine Particles: Aerosol Generation, Measurement, Sampling and Analysis, edited by Benjamin Y. H. Liu, Academic Press, New York, pp. 57–110, 1976.

T. Z. Csaky et al., Cutting's Handbook of Pharmacology, The Actions and Uses of Drugs, Seventh Edition, pp. 85–86, 285–287, 512–517, Prentice–Hall, Inc., 1984.

L. S. Goodman et al., The Pharmacological Basis of Therapeutics, Fifth Edition, Chapter 24, pp. 477–513, Chapter 29, pp. 590–629, Chapter 54, pp. 1092–1083, Chapter 70, pp. 1491, 1493, MacMillan Publishing Co., Inc., 1975.

McPherson, Steven P., Respiratory therapy equipment, Second Edition, The C. V. Mosby Company, (1981), pp. 1–32.

(List continued on next page.)

Primary Examiner—Kimberly L. Ashor

[57] ABSTRACT

A nebulizer device, comprising: (a) a housing defining an interior volume therewithin, including a reservoir portion for holding medicament therein for entrainment into a carrier gas to form a delivery gas mixture comprising nebulized medicament and carrier gas; (b) a discharge port connected to the housing in flow communication with the interior volume therewithin, for discharging the delivery gas mixture from the housing; (c) a jet passage member having (i) an inlet portion for introduction of carrier gas thereinto and (ii) a nozzle portion positioned in the interior volume of the housing for discharging carrier gas in jet form in the interior volume, for entrainment of medicament from the reservoir portion of the housing in the carrier gas jet, such nozzle portion comprising a nozzle orifice accommodating carrier gas flow therethrough, wherein the nozzle orifice has an equivalent orifice diameter in the range of from about 0.005 inch to about 0.020 inch.

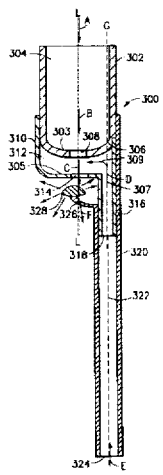

OTHER PUBLICATIONS

Pierson, David J. and Kacmarek, Robert M. *Foundations of Respiratory Care*, New York, Churchill Livingstone, pp. 793–824.

Barnes, Thomas A. et al., *Respiratory Care Practice*, Chicago, Year Book Medical Publisher, (1988), pp. 356–405.

Kacmarek, Robert M. et al., *The Essentials of Respiratory Care*, Third Edition, St. Louis, Mosby Year Book (1990), pp. 15–35, 434–438.

Benson, Jill M. et al., "The Impact of Changing Ventilator Parameters on Availability of Nebulized Drugs in an In Vitro Neonatal Lung System," *DICP, The Annals of Pharmacotherapy*, vol. 25, Mar. 1991, pp. 272–275.

McPherson, Steven P., *Respiratory Home Care Equipment*, Dubuque, Iowa, Hendall/Hunt Publishing Co., pp. 37–50.

Hanhan, Usama et al., "Effects of In–Line Nebulization on Preset Ventilatory Variables," *Respiratory Care*, vol. 38, No. 5, May 1993, pp. 474–478.

Quinn, William W., "Effect of a New Nebulizer Position on Aerosol Delivery During Mechanical Ventilation: A Bench Study," *Respiratory Care*, vol. 37, No. 5, May 1992, pp. 423–431.

McPeck, Michael et al., "Choice of Mechanical Ventilator: Influence on Nebulizer Performance," *Respiratory Care*, vol. 38, No. 8, Aug. 1993, pp. 887–895.

Rau, Joseph J., "Comparison of Nebulizer Delivery Methods through a Neonatal Endotracheal Tube: A Bench Study," *Respiratory Care*, vol. 37, No. 11, Nov. 1992, pp. 1233–1240.

Scanlan, Craig L. et al., *Egan's Fundamentals of Respiratory Care*, St. Louis, The C.V. Mosby Company (1990), pp. 52–85, 557–583.

*The European Respiratory Journal*, "Output of the Wright Jet Nebulizer", Hurst et al (letter to the ed.), Pub.=The Society and Munksgaard/Copenhagen, V3, N5, p. 608, 1990.

*The European Respiratory Journal*, "Room Temperature Influences . . . ", Kongerud et al, Pub.=The Society and Munksgaard/Copenhagen, V2, N7, pp. 681–684, 1989.

*Clinical Allergy*, "Comparison of Histamine bronchial . . . ", Beaupné et al, Blackwell Scientific Pubs, V9, pp. 575–583, 1979.

*Am. Rev. of Resp. Disease*, "Within and Between Comparison . . . ", Pison et al, Pub.=Am. Lung Assos., NY. V141, p. A837 Part 2 of 4, 1990.

*J. Aerosol. Sci.*, "Characteristics of a Double Orifice Nebulizer", Pilacinski et al, Pergamon Press PLC. V21, N7, pp. 977–982, 1990.

*Thorax*, "Jet and Ultrasonic Nebulizer Output . . . ", Dennis et al, British Med. Assoc., London,. V45, N10, pp. 728–732. Oct. 1990.

*Am. Sci. and Tech.*, "Size–Fractionating Aerosol Generator", Pilacinski et al, Elsevier Science Pub. Co., Inc. V13, pp. 450–458. 1990.

*Clinical Respiratory Physiology*, "Bronchial Challenge: A Small Reservoir for the Wright Neb.", Madsen et al, Bull. Eur. Physio. Respir., 1987, 23, 67–71.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Figure 4:
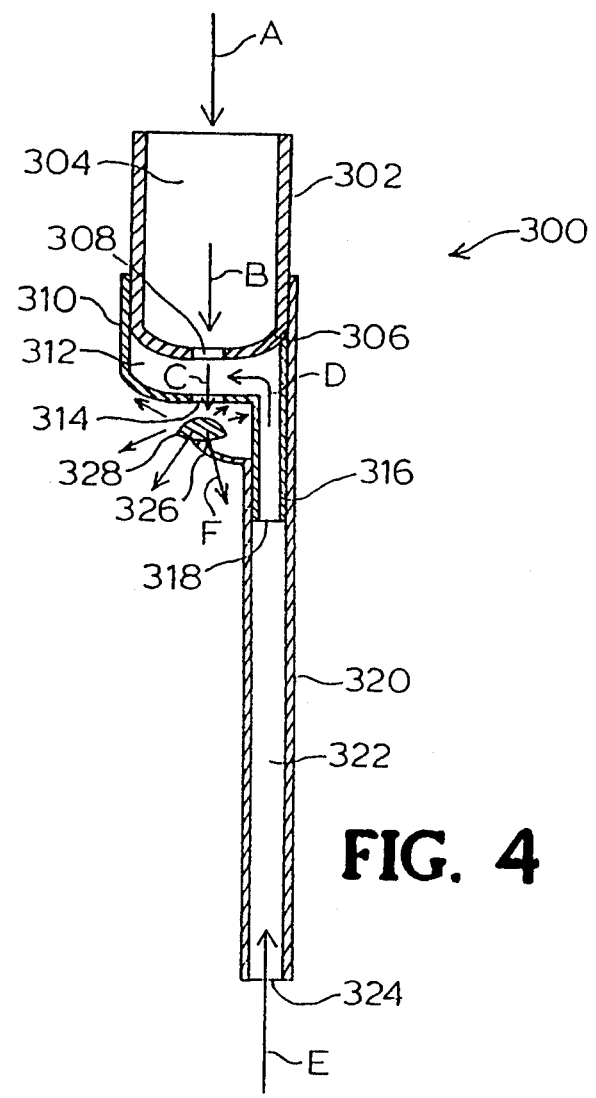

Column 12, lines 23–60:

Nebulization structure 300 includes a jet passage member 302 having an inlet portion 304 for introduction of carrier gas thereinto, such carrier gas being introduced from suitable conduit for flow control means (not shown) to effect flow of carrier gas into the inlet portion 304 of jet passage member 302 in the direction indicated by arrow A in FIG. 4 *toward the front wall 303 of the jet passage member. The jet passage member 302 has a central axis L—L as illustrated.*

Jet passage member 302 further includes a nozzle portion 306 *including front wall 303 of the jet passage member,* which is positioned in the interior volume of the nebulizer housing, for discharging carrier gas in jet form in the interior volume, through nozzle orifice 308 *in front wall 303 of the jet passage member.* The nozzle orifice *of the nozzle portion 306* has an equivalent orifice diameter in the range of from about 0.05 inch to about 0.020 inch, and preferably is from about 0.05 inch to 0.020 inch, and preferably is at least generally circular in cross-sectional shape, transverse to the flow direction indicated by arrow A *along the jet passage member axis L—L.*

By this arrangement, carrier gas passing through the jet passage member 302 flows (downwardly in the view shown) through the nozzle orifice 308 *in front wall 303 of the jet passage member 302,* in the direction indicated by arrow B (*along axis L—L*), with the carrier gas flow rate suitably being on the order of from about 1.75 to about 3.25 liters per minute.

In this embodiment of FIG. 4, the nebulization structure 300 further comprises an expansion chamber 310 in flow-receiving communication with the nozzle portion 306 of the jet passage member. The expansion *chamber* 310 defines an *enclosed* expansion volume 312 therewithin, and the expansion chamber includes an orifice 314 *in the wall 305 bounding the enclosed expansion volume 312,* through which the carrier gas is flowed in the direction indicated by arrow C (*along axis L—L*) subsequent to entrainment in such carrier gas of liquid to be nebulized, which enters the expansion volume 312 in the direction indicated by arrow D, from extension tube 316 of the expansion chamber. Expansion tube 316 has a lower open end 318 as shown, and the tube is journaled or otherwise secured in closed flow relationship to aspiration tube 320 having an interior flow passage 322 and a lower open end 324 into which liquid is aspiratingly drawn in the direction indicated by arrow E *along axis G—G of such tube. The aspirated liquid therefore moves axially upwardly in aspiration tube 320 in the view shown, and changes direction from such axial flow direction (indicated by the tail portion 307 of arrow D), to a transverse or generally horizontal direction (indicated by head 309 of arrow D). In this manner, the aspirated liquid is* flowed *transversely across the interior expansion volume 312 of expansion chamber 310, so that the transversely flowed liquid then is contacted with the axially flowing carrier gas flowed sequentially through nozzle portion 306, orifice 308 and orifice 314 in expansion chamber wall 305. By this arrangement, the aspirated liquid is confined between the generally parallel but spaced-apart walls 303 and 305, to provide entrainment of the axially flowing carrier gas.*

*As shown, the orifices 308, 314 and impingement baffle 328 are all coaxially aligned along axis L—L. Further, such axis L—L is parallel to the axis G—G of the liquid aspiration tube 320.*

THE DRAWING FIGURES HAVE BEEN CHANGED AS FOLLOWS:

Reference numerals 303, 305, 307, and 309 have been added, as well as extended axes to FIG. 4.

AS A RESULT OF REEXAMINATION, IT HAS BEEN DETERMINED THAT:

Claims 1–6, 8–10 and 14 are determined to be patentable as amended.

Claims 7 and 11–13, dependent on an amended claim, are determined to be patentable.

New claims 15–33 are added and determined to be patentable.

1. A small volume nebulizer device, comprising:
   (a) a housing defining a nebulizer receptacle having an interior volume therewithin, including a reservoir portion for holding medicament therein for entrainment into a carrier gas to form a delivery gas mixture comprising nebulized medicament and carrier gas, said nebulizer receptacle having a size defining said nebulizer device as a small volume nebulizer device;
   (b) a discharge port connected to the hou ing in flow communication with the interior volume therein, for discharging the delivery gas mixture from the housing;
   (c) means for increasing delivery of pulmonarily effective aerosol particles at low flow rates through said nebulizer receptacle, comprising:
      a jet passage member having (i) an inlet means for introduction of carrier gas thereinto and (ii) nozzle means positioned in the interior volume of the housing for discharging carrier gas in jet form into the interior volume of said nebulizer receptacle for entrainment of medicament from the reservoir portion of the housing in the carrier gas jet, said nozzle means comprising a nozzle portion *having a cross section transverse to the direction of gas flow through the jet passage member, and* comprising a nozzle orifice *at an extremity of the nozzle portion,* accommodating carrier gas flow therethrough, wherein the nozzle orifice has an equivalent orifice diameter in the range of from about 0.005 inch to about 0.015 inch;
   (d) *an expansion chamber joined to the nozzle portion of the jet passage member, said expansion chamber being coextensive in cross-sectional transverse extent with the nozzle portion of the jet passage member, and including an expansion chamber wall which is spaced in the direction of gas flow from the nozzle portion to* define an enclosed expansion volume therebetween, said expansion chamber wall having an orifice therein which is in alignment with the orifice of the nozzle portion;

(e) a vertically extending aspiration tube in the interior volume of the housing, having a lower open end, and an upper end joined in flow communication with the expansion chamber so that in operation fluid upwardly drawn through the aspiration tube is flowed transversely across the enclosed expansion volume for entrainment in gas flowed in the jet passage member through the orifice of the nozzle portion and the orifice in the expansion chamber wall, to form said delivery gas mixture;

(f) an impingement baffle presenting an impingement surface in alignment with the orifice of the jet passage member, to receive the delivery gas mixture and disperse same in the interior volume of the housing for discharge from the housing through the discharge port; and (g) pressurized carrier gas supply means coupled in gas-supplying relationship with the inlet portion of the jet *flow* passage member, for supplying pressurized carrier gas at a flow rate of from about 0.5 to 2.8 liters per minute.

2. A device according to claim 1, wherein the equivalent orifice diameter *of the nozzle orifice* is in the range of from 0.008 inch to 0.015 inch.

3. A device according to claim 1, wherein the equivalent orifice diameter *of the nozzle orifice* is in the range of from 0.010 inch to 0.012 inch.

4. A device according to claim 1, [further comprising a nebulization structure mounted in the interior volume of the housing, including: an] *wherein the* expansion chamber [in flow-receiving communication] *is vertically coaxially aligned* with the nozzle portion of the jet passage member, and said [expansion chamber having an orifice therein, in alignment with the orifice of the jet passage member; said impingement baffle presenting an impingement surface in alignment with the orifices of both the jet passage member and the expansion chamber; and means for aspiratingly delivering liquid from the reservoir portion of the housing when liquid is contained in the reservoir and] carrier gas is flowed *downwardly* in sequence through the orifices of the *nozzle portion of the* jet passage member and the expansion chamber [at sufficient volumetric flow rate] *while fluid drawn upwardly through the aspiration tube to the expansion chamber is flowed horizontally across the enclosed expansion volume.*

5. A device according to claim 4, wherein the orifice in the expansion chamber *wall* has an equivalent orifice diameter in the range of from 0.025 inch to 0.060 inch.

6. A device according to claim 4, wherein the orifice in the expansion chamber *wall* has an equivalent orifice diameter in the range of from 0.030 inch to 0.050 inch.

8. A device according to claim 1, [further comprising means disposed in] *wherein the* aspiration tube *extends vertically downwardly* to a lower portion of the interior volume of the housing for delivering liquid from the reservoir portion of the housing to [a discharge locus] *to the expansion chamber when carrier gas is flowed through* [of] the nozzle orifice of the jet passage member, whereby delivered liquid is entrained in carrier gas flowed through the jet passage member *nozzle orifice and orifice in the expansion chamber wall* when the reservoir portion contains liquid.

9. A method of delivering a nebulized medicament to a patient, and increasing delivery of pulmonarily effective aerosol particles at low flow rates comprising the steps of:

(I) providing a nebulizer apparatus including a breathing circuit coupled to the patient and including a small volume nebulizer device, wherein the small volume nebulizer device comprises:

(a) a housing defining a nebulizer receptacle having an interior volume therewithin, including a reservoir portion for holding medicament therein for entrainment into a carrier gas to form a delivery gas mixture comprising nebulized medicament and carrier gas, said nebulizer receptacle having a size defining said nebulizer device as a small volume nebulizer device;

(b) a discharge port connected to the housing in flow communication with the interior volume [therewithin] *therewithin*, for discharging the delivery gas mixture from the housing;

(c) means for increasing delivery of pulmonarily effective aerosol particles at low flow rates through said nebulizer receptacle, comprising:

a jet passage member having (i) an inlet means for introduction of carrier gas thereinto and (ii) a nozzle means positioned in the interior volume of the housing for discharging carrier gas in jet form into the interior volume of said nebulizer receptacle, for entrainment of medicament from the reservoir portion of the housing in the carrier gas jet, said nozzle *means comprising a nozzle portion having a cross-section transversed to the direction of gas flow through the jet passage member, and* comprising a nozzle orifice [comprising a nozzle orifice] *at an extremity of the nozzle portion,* accommodating carrier gas flow therethrough, wherein the nozzle orifice has an equivalent orifice diameter in the range of from about 0.005 inch to about 0.015 inch;

(d) *an expansion chamber joined to the nozzle portion of the jet passage member, said expansion chamber being coextensive in cross-sectional transverse extent with the nozzle portion of the jet passage member, and including an expansion chamber wall which is spaced in the direction of gas flow from the nozzle portion to define an enclosed expansion volume therebetween, said expansion chamber wall having an orifice therein which is in alignment with the orifice of the nozzle portion;*

(e) *a vertically extending aspiration tube in the interior volume of the housing, having a lower open end and an upper end joined in flow communication with the expansion chamber so that in operation fluid upwardly drawn through the aspiration tube is flowed transversely across the enclosed expansion volume for entrainment in gas flowed in the jet passage member through the orifice of the nozzle portion and the orifice in the expansion chamber wall, to form said delivery gas mixture;* and (f) an impingement baffle presenting an impingement surface in alignment with the orifice of the jet passage member, *to receive the delivery gas mixture and disperse same in the interior volume of the housing for discharge from the housing through the discharge port*;

(II) disposing a medicament in the reservoir portion of the housing;

(III) flowing the carrier gas through the jet passage member of the jet nebulizer device and nebulizer receptacle at a flow rate in the range of from about 0.5 to 2.8 liters per minute *while aspirating medicament* from the reservoir to cause medicament to flow through the aspiration tube from the lower open end thereof to the enclosed expansion volume of the expansion chamber for transverse flow across the expansion volume for contact with and entrainment in the carrier gas flowed through the nozzle orifice and expansion chamber wall orifice, to disperse the medicament into the carrier gas and form a pulmonarily effective nebulized [medicament] *medicant* in the carrier gas, as a medicant/carrier gas mixture; and (IV) passing the medicament/carrier gas mixture through the breathing circuit to a pulmonary situs of the patient.

10. A method according to claim 9, comprising flowing the carrier gas *at a* flow rate in range of from 1.0 to 2.8 liters per minute.

14. A method according to claim 9, comprising providing the *nozzle orifice with an* equivalent orifice diameter in the range of from 0.007 inch to 0.018 inch.

15. *A device according to claim 1, wherein the nebulizer receptacle is formed of a synthetic resinous material.*

16. *A device according to claim 15, wherein the synthetic resinous material is transparent.*

17. *A device according to claim 15, wherein the synthetic resinous material is a thermoplastic.*

18. *A device according to claim 15, wherein the synthetic resinous material is selected from the group consisting of polyolefins and polyvinyl chlorides.*

19. *A small volume nebulizer device for delivery of a medicament to a patient, comprising:*

(a) *a housing defining a nebulizer receptacle having an interior volume therewithin, including a reservoir portion for holding medicament therein for entrainment into a carrier gas to form a delivery gas mixture comprising nebulized medicament and carrier gas, said nebulizer receptacle having a side defining said nebulizer device as a small volume nebulizer device;*

(b) *a discharge port connected to the housing in flow communication with the interior volume therein, for discharging the delivery gas mixture from the housing;*

(c) *means for increasing delivery of pulmonarily effective aerosol particles at low flow rates through said nebulizer receptacle, comprising:*

*a jet passage member having (i) an inlet means for introduction of carrier gas thereinto and (ii) a nozzle means positioned in the interior volume of the housing for discharging carrier gas in jet form into the interior volume of said nebulizer receptacle for entrainment of medicament from the reservoir portion of the housing in the carrier gas jet, said nozzle means comprising a nozzle portion having a cross-section transverse to the direction of gas flow through the jet passage member, and comprising a nozzle orifice at an extremity of the nozzle portion accommodating carrier gas flow therethrough, wherein the nozzle orifice has an equivalent orifice diameter in the range of from about 0.005 inch to about 0.015 inch;*

(d) *an expansion chamber joined to the nozzle portion of the jet passage member, said expansion chamber being cross-sectionally coextensive with the nozzle portion of the jet passage member;*

(e) *a vertically extending aspiration tube in the interior volume of the housing, having a lower open end, and an upper end joined in flow communication with the expansion chamber so that in operation fluid upwardly drawn through the aspiration tube is flowed transversely across the enclosed expansion volume for entrainment in gas flowed in the jet passage member through the orifice of the nozzle portion and the orifice in the expansion chamber wall, to form said delivery gas mixture;*

(f) *an impingement baffle presenting an impingement surface in alignment with the orifice of the jet passage member, to receive the delivery gas mixture and disperse same in the interior volume of the housing for discharge from the housing through the discharge port; and*

*pressurized carrier gas supply means coupled in gas-supplying relationship with the inlet portion of the jet passage member, for supplying pressurized carrier gas at a flow rate of from about 0.5 to 2.8 liters per minute;*

*a nebulization structure mounted in the interior volume of the housing, including:*

*said expansion chamber being coaxial with the jet passage member and cross-sectionally coextensive therewith, to define an enclosed expansion volume in flow receiving communication with the nozzle portion of the jet passage member, said expansion chamber having an orifice therein, in coaxial alignment with the orifice of the jet passage member;*

*said impingement baffle presenting an impingement surface in alignment with the orifice of the expansion chamber; and*

*means for aspiratingly delivering liquid from the reservoir portion of the housing to a discharge locus of the nozzle orifice of the jet passage member when liquid is contained in the reservoir portion and carrier gas is flowed in sequence through the orifices of the jet passage member and the expansion chamber at sufficient volumetric flow rate, comprising an aspiration tube with an interior flow passage, said aspiration tube having a lower end in the reservoir portion of the housing and an upper end joined in liquid flow discharge relationship to said expansion chamber, for aspiratingly drawing liquid from the reservoir portion through the interior flow passage into the expansion chamber when liquid is contained in the reservoir portion and carrier gas is flowed in sequence through the orifices of the jet passage member and the expression chamber at sufficient volumetric flow rates whereby delivered liquid is flowed in the aspiration tube to the expansion chamber for transverse flow perpendicular to the direction of gas flow through the orifice of the nozzle portion of the jet passage member and the orifice of the expansion chamber, so that the transversely flowed liquid is contacted with gas from the nozzle portion orifice and so that the liquid is entrained in carrier gas flowed through the jet passage member and expansion chamber when the reservoir portion contains liquid.*

20. *A device according to claim 19, wherein the equivalent orifice diameter of the nozzle portion orifice is in the range of from 0.008 inch to 0.015 inch.*

21. *A device according to claim 19, wherein the equivalent orifice diameter of the nozzle portion orifice is in the range of from 0.010 inch to 0.012 inch.*

22. *A device according to claim 19, wherein the orifice in the expansion chamber has an equivalent orifice diameter in the range of from 0.025 inch to 0.060 inch.*

23. *A device according to claim 19, wherein the orifice in the expansion chamber has an equivalent orifice diameter in the range of from 0.030 inch to 0.050 inch.*

24. A device according to claim 19, further comprising a breathing circuit coupled with the discharge port for receiving delivery gas mixture and conveying same to a patient interconnected with the breathing circuit.

25. A device according to claim 19, wherein the jet passage member nozzle orifice, expansion chamber orifice and impingement surface of said impingement baffle are all vertically axially aligned with one another.

26. A device according to claim 25, wherein the aspiration tube is vertically aligned with a vertical axis which is parallel to the axis of the vertically axially aligned jet passage member orifice, expansion chamber orifice and impingement surface of said impingement baffle.

27. A device according to claim 26, wherein liquid aspiratingly drawn from the reservoir portion through the interior flow passage into the expansion chamber is discharged substantially horizontally for entrainment into downwardly vertically flowing carrier gas discharged from the jet member orifice.

28. A device according to claim 1, wherein the impingement baffle comprises a convex impingement surface.

29. A device according to claim 1, wherein said impingement surface of said impingement baffle is symmetrical about a vertical axis aligned with a central axis of said orifice of said nozzle portion of said passage member.

30. A device according to claim 19, wherein the nebulizer receptacle is formed of a synthetic resinous material.

31. A device according to claim 30, wherein the synthetic resinous material is transparent.

32. A device according to claim 30, wherein the synthetic resinous material is a thermoplastic.

33. A device according to claim 30, wherein the synthetic resinous material is selected from the group consisting of polyolefins and polyvinyl chlorides.

* * * * *